(12) United States Patent
Hacohen

(10) Patent No.: US 11,109,964 B2
(45) Date of Patent: Sep. 7, 2021

(54) AXIALLY-SHORTENING PROSTHETIC VALVE

(71) Applicant: CARDIOVALVE LTD., Or Yehuda (IL)

(72) Inventor: Gil Hacohen, Ramat Gan (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/138,129

(22) Filed: Sep. 21, 2018

(65) Prior Publication Data

US 2019/0015202 A1 Jan. 17, 2019

Related U.S. Application Data

(60) Continuation of application No. 15/729,107, filed on Oct. 10, 2017, now abandoned, which is a
(Continued)

(51) Int. Cl.
*A61F 2/24* (2006.01)
*A61B 17/04* (2006.01)
(Continued)

(52) U.S. Cl.
CPC ........ *A61F 2/2418* (2013.01); *A61B 17/0401* (2013.01); *A61B 17/064* (2013.01);
(Continued)

(58) Field of Classification Search
CPC .......................................................... A61F 2/24
See application file for complete search history.

(56) References Cited

U.S. PATENT DOCUMENTS 3,874,388 A 4/1975 King et al.
4,222,126 A 9/1980 Boretos et al.
(Continued)

FOREIGN PATENT DOCUMENTS

CA 2822801 8/2006
CN 103942537 A 7/2014
(Continued)

OTHER PUBLICATIONS

An Advisory Action dated Apr. 2, 2018, which issued during the prosecution of U.S. Appl. No. 14/763,004.
(Continued)

*Primary Examiner* — Jacqueline Woznicki
(74) *Attorney, Agent, or Firm* — Sughrue Mion, PLLC

(57) ABSTRACT

A catheter is transluminally advanced to a heart of a subject. Via the catheter, a prosthetic valve is advanced to the native valve. The prosthetic valve includes an upstream skirt, and a downstream skirt that has a first portion and a second portion. The first portion defines a lumen therethrough. The second portion circumscribes the first portion, and defines a plurality of anchoring arms that are coupled to the second portion. A plurality of prosthetic leaflets, within the lumen, are attached to the first portion. The upstream skirt is expanded in the atrium, and the anchoring arms are expanded in the ventricle, the anchoring arms extending radially outward and toward the upstream skirt. Subsequently, native valve tissue is squeezed between the upstream skirt and the anchoring arms by causing the anchoring arms to move with respect to the prosthetic leaflets, and toward the upstream skirt.

14 Claims, 16 Drawing Sheets

Related U.S. Application Data continuation of application No. 14/626,267, filed on Feb. 19, 2015, now Pat. No. 9,788,941, which is a division of application No. 13/044,694, filed on Mar. 10, 2011, now abandoned.

(60) Provisional application No. 61/312,412, filed on Mar. 10, 2010.

(51) Int. Cl.
  *A61B 17/064* (2006.01)
  *A61B 17/00* (2006.01)

(52) U.S. Cl.
  CPC .......... *A61F 2/2409* (2013.01); *A61F 2/2427* (2013.01); *A61F 2/2436* (2013.01); *A61F 2/2457* (2013.01); *A61B 2017/00243* (2013.01); *A61B 2017/0414* (2013.01); *A61B 2017/0441* (2013.01); *A61B 2017/0464* (2013.01); *A61B 2017/0649* (2013.01); *A61F 2220/0016* (2013.01); *A61F 2230/005* (2013.01); *A61F 2230/0054* (2013.01); *A61F 2230/0078* (2013.01); *A61F 2250/0063* (2013.01)

(56) References Cited

U.S. PATENT DOCUMENTS

| | | | |
|---|---|---|---|
| 4,261,342 A | 4/1981 | Aranguren Duo | |
| 4,340,091 A | 7/1982 | Skelton et al. | |
| 4,423,525 A | 1/1984 | Vallana et al. | |
| 4,853,986 A | 8/1989 | Allen | |
| 4,892,541 A | 1/1990 | Alonso | |
| 4,972,494 A | 11/1990 | White et al. | |
| 5,108,420 A | 4/1992 | Marks | |
| 5,314,473 A | 5/1994 | Godin | |
| 5,405,378 A | 4/1995 | Strecker | |
| 5,443,500 A | 8/1995 | Sigwart | |
| 5,607,444 A | 3/1997 | Lam | |
| 5,607,470 A | 3/1997 | Milo | |
| 5,647,857 A | 7/1997 | Anderson et al. | |
| 5,713,948 A | 2/1998 | Uflacker | |
| 5,716,417 A | 2/1998 | Girard et al. | |
| 5,741,297 A | 4/1998 | Simon | |
| 5,765,682 A | 6/1998 | Bley et al. | |
| 5,776,140 A | 7/1998 | Cottone | |
| 5,868,777 A | 2/1999 | Lam | |
| 5,873,906 A | 2/1999 | Lau et al. | |
| 5,954,766 A | 9/1999 | Zadno-Azizi et al. | |
| 5,957,949 A | 9/1999 | Leonhardt et al. | |
| 5,980,565 A | 11/1999 | Jayaraman | |
| 6,010,530 A | 1/2000 | Goicoechea | |
| 6,019,787 A | 2/2000 | Richard et al. | |
| 6,042,607 A | 3/2000 | Williamson, IV et al. | |
| 6,074,417 A | 6/2000 | Peredo | |
| 6,113,612 A | 9/2000 | Swanson et al. | |
| 6,120,534 A | 9/2000 | Ruiz | |
| 6,152,937 A | 11/2000 | Peterson et al. | |
| 6,165,183 A | 12/2000 | Kuehn et al. | |
| 6,165,210 A | 12/2000 | Lau et al. | |
| 6,187,020 B1 | 2/2001 | Zegdi et al. | |
| 6,193,745 B1 | 2/2001 | Fogarty et al. | |
| 6,264,700 B1 | 7/2001 | Kilcoyne et al. | |
| 6,287,339 B1 | 9/2001 | Vazquez et al. | |
| 6,312,465 B1 | 11/2001 | Griffin et al. | |
| 6,332,893 B1 | 12/2001 | Mortier et al. | |
| 6,334,873 B1 | 1/2002 | Lane et al. | |
| 6,346,074 B1 | 2/2002 | Roth | |
| 6,350,278 B1 | 2/2002 | Lenker et al. | |
| 6,352,561 B1 | 3/2002 | Leopold et al. | |
| 6,391,036 B1 | 5/2002 | Berg et al. | |
| 6,402,780 B2 | 6/2002 | Williamson, IV et al. | |
| 6,409,755 B1 | 6/2002 | Vrba | |
| 6,419,696 B1 | 7/2002 | Ortiz et al. | |
| 6,428,550 B1 | 8/2002 | Vargas et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,511,491 B2 | 1/2003 | Grudem et al. | |
| 6,530,952 B2 | 3/2003 | Vesely | |
| 6,540,782 B1 | 4/2003 | Snyders | |
| 6,551,350 B1 | 4/2003 | Thornton et al. | |
| 6,558,396 B1 | 5/2003 | Inoue | |
| 6,558,418 B2 | 5/2003 | Carpentier et al. | |
| 6,569,196 B1 | 5/2003 | Vesely | |
| 6,602,263 B1 | 8/2003 | Swanson et al. | |
| 6,616,675 B1 | 9/2003 | Evard et al. | |
| 6,652,556 B1 | 11/2003 | VanTassel et al. | |
| 6,669,724 B2 | 12/2003 | Park et al. | |
| 6,682,558 B2 | 1/2004 | Tu et al. | |
| 6,699,256 B1 | 3/2004 | Logan et al. | |
| 6,716,244 B2 | 4/2004 | Klaco | |
| 6,719,781 B1 | 4/2004 | Kim | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,752,813 B2 | 6/2004 | Goldfarb et al. | |
| 6,764,518 B2 | 7/2004 | Godin | |
| 6,767,362 B2 | 7/2004 | Schreck | |
| 6,797,002 B2 | 9/2004 | Spence et al. | |
| 6,821,297 B2 | 11/2004 | Snyders | |
| 6,830,585 B1 | 12/2004 | Artof et al. | |
| 6,830,638 B2 | 12/2004 | Boylan et al. | |
| 6,893,460 B2 | 5/2005 | Spenser et al. | |
| 6,926,715 B1 | 8/2005 | Hauck et al. | |
| 6,960,217 B2 | 11/2005 | Bolduc | |
| 6,964,684 B2 | 11/2005 | Ortiz et al. | |
| 6,974,476 B2 | 12/2005 | McGuckin, Jr. et al. | |
| 7,011,681 B2 | 3/2006 | Vesely | |
| 7,018,406 B2 | 3/2006 | Seguin et al. | |
| 7,041,132 B2 | 5/2006 | Quijano et al. | |
| 7,077,861 B2 | 7/2006 | Spence | |
| 7,101,395 B2 | 9/2006 | Tremulis et al. | |
| 7,101,396 B2 | 9/2006 | Artof et al. | |
| 7,137,184 B2 | 11/2006 | Schreck | |
| 7,172,625 B2 | 2/2007 | Shu et al. | |
| 7,198,646 B2 | 4/2007 | Figulla et al. | |
| 7,201,772 B2 | 4/2007 | Schwammenthal et al. | |
| 7,226,467 B2 | 6/2007 | Lucatero et al. | |
| 7,226,477 B2 | 6/2007 | Cox | |
| 7,288,097 B2 | 10/2007 | Séguin | |
| 7,288,111 B1 | 10/2007 | Holloway et al. | |
| 7,316,716 B2 | 1/2008 | Egan | |
| 7,329,279 B2 | 2/2008 | Haug et al. | |
| 7,335,213 B1 | 2/2008 | Hyde et al. | |
| 7,351,256 B2 | 4/2008 | Hojeibane et al. | |
| 7,374,573 B2 | 5/2008 | Gabbay | |
| 7,377,938 B2 | 5/2008 | Sarac et al. | |
| 7,381,218 B2 | 6/2008 | Schreck | |
| 7,381,219 B2 | 6/2008 | Salahieh et al. | |
| 7,404,824 B1 | 7/2008 | Webler et al. | |
| 7,422,603 B2 | 9/2008 | Lane | |
| 7,429,269 B2 | 9/2008 | Schwammenthal et al. | |
| 7,442,204 B2 | 10/2008 | Schwammenthal et al. | |
| 7,445,630 B2 | 11/2008 | Lashinski et al. | |
| 7,455,677 B2 | 11/2008 | Vargas et al. | |
| 7,455,688 B2 | 11/2008 | Furst et al. | |
| 7,462,162 B2 | 12/2008 | Phan et al. | |
| 7,481,838 B2 | 1/2009 | Carpentier et al. | |
| 7,510,575 B2 | 3/2009 | Spenser et al. | |
| 7,513,909 B2 | 4/2009 | Lane et al. | |
| 7,524,331 B2 | 4/2009 | Birdsall | |
| 7,527,646 B2 | 5/2009 | Rahdert et al. | |
| 7,556,632 B2 | 7/2009 | Zadno | |
| 7,556,646 B2 | 7/2009 | Yang et al. | |
| 7,563,267 B2 | 7/2009 | Goldfarb et al. | |
| 7,563,273 B2 | 7/2009 | Goldfarb et al. | |
| 7,582,111 B2 | 9/2009 | Krolik et al. | |
| 7,585,321 B2 | 9/2009 | Cribier | |
| 7,597,711 B2 | 10/2009 | Drews et al. | |
| 7,608,091 B2 | 10/2009 | Goldfarb et al. | |
| 7,611,534 B2 | 11/2009 | Kapadia et al. | |
| 7,621,948 B2 | 11/2009 | Herrmann et al. | |

(56) References Cited

U.S. PATENT DOCUMENTS

| | | | |
|---|---|---|---|
| 7,625,403 | B2 | 12/2009 | Krivoruchko |
| 7,632,302 | B2 | 12/2009 | Vreeman et al. |
| 7,635,329 | B2 | 12/2009 | Goldfarb et al. |
| 7,648,528 | B2 | 1/2010 | Styrc |
| 7,655,015 | B2 | 2/2010 | Goldfarb et al. |
| 7,682,380 | B2 | 3/2010 | Thornton et al. |
| 7,708,775 | B2 | 5/2010 | Rowe et al. |
| 7,717,952 | B2 | 5/2010 | Case et al. |
| 7,717,955 | B2 | 5/2010 | Lane et al. |
| 7,731,741 | B2 | 6/2010 | Eidenschink |
| 7,736,388 | B2 | 6/2010 | Goldfarb et al. |
| 7,748,389 | B2 | 7/2010 | Salahieh et al. |
| 7,753,922 | B2 | 7/2010 | Starksen |
| 7,758,595 | B2 | 7/2010 | Allen et al. |
| 7,758,632 | B2 | 7/2010 | Hojeibane et al. |
| 7,758,640 | B2 | 7/2010 | Vesely |
| 7,771,467 | B2 | 8/2010 | Svensson |
| 7,771,469 | B2 | 8/2010 | Liddicoat |
| 7,776,083 | B2 | 8/2010 | Vesely |
| 7,780,726 | B2 | 8/2010 | Seguin |
| 7,799,069 | B2 | 9/2010 | Bailey et al. |
| 7,803,181 | B2 | 9/2010 | Furst et al. |
| 7,811,296 | B2 | 10/2010 | Goldfarb et al. |
| 7,811,316 | B2 | 10/2010 | Kalmann et al. |
| 7,824,442 | B2 | 11/2010 | Salahieh et al. |
| 7,837,645 | B2 | 11/2010 | Bessler et al. |
| 7,837,727 | B2 | 11/2010 | Goetz et al. |
| 7,842,081 | B2 | 11/2010 | Yadin |
| 7,850,725 | B2 | 12/2010 | Vardi et al. |
| 7,871,432 | B2 | 1/2011 | Bergin |
| 7,871,436 | B2 | 1/2011 | Ryan et al. |
| 7,887,583 | B2 | 2/2011 | Macoviak |
| 7,892,281 | B2 | 2/2011 | Seguin et al. |
| 7,896,915 | B2 | 3/2011 | Guyenot et al. |
| 7,914,544 | B2 | 3/2011 | Nguyen et al. |
| 7,914,569 | B2 | 3/2011 | Nguyen et al. |
| 7,927,370 | B2 | 4/2011 | Webler et al. |
| 7,942,927 | B2 | 5/2011 | Kaye et al. |
| 7,947,072 | B2 | 5/2011 | Yang et al. |
| 7,947,075 | B2 | 5/2011 | Goetz et al. |
| 7,951,195 | B2 | 5/2011 | Antonsson et al. |
| 7,955,375 | B2 | 6/2011 | Agnew |
| 7,955,377 | B2 | 6/2011 | Melsheimer |
| 7,955,384 | B2 | 6/2011 | Rafiee et al. |
| 7,959,666 | B2 | 6/2011 | Salahieh et al. |
| 7,959,672 | B2 | 6/2011 | Salahieh et al. |
| 7,967,833 | B2 | 6/2011 | Sterman et al. |
| 7,967,857 | B2 | 6/2011 | Lane |
| 7,981,151 | B2 | 7/2011 | Rowe |
| 7,981,153 | B2 | 7/2011 | Fogarty et al. |
| 7,992,567 | B2 | 8/2011 | Hirotsuka et al. |
| 7,993,393 | B2 | 8/2011 | Carpentier et al. |
| 8,002,825 | B2 | 8/2011 | Letac et al. |
| 8,002,826 | B2 | 8/2011 | Seguin |
| 8,016,877 | B2 | 9/2011 | Seguin et al. |
| 8,016,882 | B2 | 9/2011 | Macoviak et al. |
| 8,021,420 | B2 | 9/2011 | Dolan |
| 8,021,421 | B2 | 9/2011 | Fogarty et al. |
| 8,025,695 | B2 | 9/2011 | Fogarty et al. |
| 8,029,518 | B2 | 10/2011 | Goldfarb et al. |
| 8,029,557 | B2 | 10/2011 | Sobrino-Serrano et al. |
| 8,029,564 | B2 | 10/2011 | Johnson et al. |
| 8,034,104 | B2 | 10/2011 | Carpentier et al. |
| 8,038,720 | B2 | 10/2011 | Wallace et al. |
| 8,043,360 | B2 | 10/2011 | McNamara et al. |
| 8,048,138 | B2 | 11/2011 | Sullivan et al. |
| 8,048,140 | B2 | 11/2011 | Purdy |
| 8,048,153 | B2 | 11/2011 | Salahieh et al. |
| 8,052,592 | B2 | 11/2011 | Goldfarb et al. |
| 8,052,741 | B2 | 11/2011 | Bruszewski et al. |
| 8,052,749 | B2 | 11/2011 | Salahieh et al. |
| 8,057,493 | B2 | 11/2011 | Goldfarb et al. |
| 8,057,532 | B2 | 11/2011 | Hoffman |
| 8,057,540 | B2 | 11/2011 | Letac et al. |
| 8,062,355 | B2 | 11/2011 | Figulla et al. |
| 8,062,359 | B2 | 11/2011 | Marquez et al. |
| 8,070,708 | B2 | 12/2011 | Rottenberg et al. |
| 8,070,800 | B2 | 12/2011 | Lock et al. |
| 8,070,802 | B2 | 12/2011 | Lamphere et al. |
| 8,070,804 | B2 | 12/2011 | Hyde et al. |
| 8,075,611 | B2 | 12/2011 | Millwee et al. |
| 8,080,054 | B2 | 12/2011 | Rowe |
| 8,083,793 | B2 | 12/2011 | Lane et al. |
| D652,927 | S | 1/2012 | Braido et al. |
| D653,341 | S | 1/2012 | Braido et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,105,377 | B2 | 1/2012 | Liddicoat |
| 8,109,996 | B2 | 2/2012 | Stacchino et al. |
| 8,118,866 | B2 | 2/2012 | Herrmann et al. |
| 8,133,270 | B2 | 3/2012 | Kheradvar et al. |
| 8,136,218 | B2 | 3/2012 | Millwee et al. |
| 8,137,398 | B2 | 3/2012 | Tuval et al. |
| 8,142,492 | B2 | 3/2012 | Forster et al. |
| 8,142,494 | B2 | 3/2012 | Rahdert et al. |
| 8,142,496 | B2 | 3/2012 | Berreklouw |
| 8,142,497 | B2 | 3/2012 | Friedman |
| 8,147,504 | B2 | 4/2012 | Ino et al. |
| 8,157,852 | B2 | 4/2012 | Bloom et al. |
| 8,157,853 | B2 | 4/2012 | Laske et al. |
| 8,157,860 | B2 | 4/2012 | McNamara et al. |
| 8,163,008 | B2 | 4/2012 | Wilson et al. |
| 8,163,014 | B2 | 4/2012 | Lane et al. |
| D660,433 | S | 5/2012 | Braido et al. |
| D660,967 | S | 5/2012 | Braido et al. |
| 8,167,894 | B2 | 5/2012 | Miles et al. |
| 8,167,932 | B2 | 5/2012 | Bourang et al. |
| 8,167,935 | B2 | 5/2012 | McGuckin, Jr. et al. |
| 8,172,896 | B2 | 5/2012 | McNamara et al. |
| 8,172,898 | B2 | 5/2012 | Alferness et al. |
| 8,177,836 | B2 | 5/2012 | Lee et al. |
| 8,182,528 | B2 | 5/2012 | Salahieh et al. |
| 8,211,169 | B2 | 7/2012 | Lane et al. |
| 8,216,256 | B2 | 7/2012 | Raschdorf, Jr. et al. |
| 8,216,301 | B2 | 7/2012 | Bonhoeffer et al. |
| 8,221,492 | B2 | 7/2012 | Case et al. |
| 8,221,493 | B2 | 7/2012 | Boyle et al. |
| 8,226,710 | B2 | 7/2012 | Nguyen et al. |
| 8,231,670 | B2 | 7/2012 | Salahieh et al. |
| 8,236,045 | B2 | 8/2012 | Benichou et al. |
| 8,236,049 | B2 | 8/2012 | Rowe et al. |
| 8,252,042 | B2 | 8/2012 | McNamara et al. |
| 8,252,051 | B2 | 8/2012 | Chau et al. |
| 8,252,052 | B2 | 8/2012 | Salahieh et al. |
| 8,257,390 | B2 | 9/2012 | Carley et al. |
| 8,267,988 | B2 | 9/2012 | Hamer et al. |
| 8,277,501 | B2 | 10/2012 | Chalekian et al. |
| 8,287,591 | B2 | 10/2012 | Keidar et al. |
| 8,298,280 | B2 | 10/2012 | Yadin et al. |
| 8,303,653 | B2 | 11/2012 | Bonhoeffer et al. |
| 8,308,798 | B2 | 11/2012 | Pintor et al. |
| 8,317,853 | B2 | 11/2012 | Agnew |
| 8,317,855 | B2 | 11/2012 | Gregorich et al. |
| 8,323,335 | B2 | 12/2012 | Rowe et al. |
| 8,328,868 | B2 | 12/2012 | Paul et al. |
| 8,337,541 | B2 | 12/2012 | Quadri et al. |
| 8,343,174 | B2 | 1/2013 | Goldfarb et al. |
| 8,343,213 | B2 | 1/2013 | Salahieh et al. |
| 8,348,999 | B2 | 1/2013 | Kheradvar et al. |
| 8,366,767 | B2 | 2/2013 | Zhang |
| 8,372,140 | B2 | 2/2013 | Hoffman et al. |
| 8,377,119 | B2 | 2/2013 | Drews et al. |
| 8,398,708 | B2 | 3/2013 | Meiri et al. |
| 8,403,981 | B2 | 3/2013 | Forster et al. |
| 8,403,983 | B2 | 3/2013 | Quadri et al. |
| 8,408,214 | B2 | 4/2013 | Spenser |
| 8,414,644 | B2 | 4/2013 | Quadri et al. |
| 8,425,593 | B2 | 4/2013 | Braido et al. |
| 8,430,934 | B2 | 4/2013 | Das |
| 8,444,689 | B2 | 5/2013 | Zhang |
| 8,449,599 | B2 | 5/2013 | Chau et al. |
| 8,449,625 | B2 | 5/2013 | Campbell et al. |
| 8,454,686 | B2 | 6/2013 | Alkhatib |

(56) References Cited

U.S. PATENT DOCUMENTS

| | | |
|---|---|---|
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray, III et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 3,034,033 A1 | 5/2015 | McLean et al. |
| 9,023,100 B2 | 5/2015 | Quadri et al. |
| 9,034,032 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich, Jr. et al. |
| 9,060,858 B2 | 6/2015 | Thornton et al. |
| 9,072,603 B2 | 7/2015 | Tuval et al. |
| 9,084,676 B2 | 7/2015 | Chau et al. |
| 9,095,434 B2 | 8/2015 | Rowe |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,659 B2 | 11/2015 | Bodewadt et al. |
| 9,173,738 B2 | 11/2015 | Murray, III et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman, III et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford, III et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keranen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,770,256 B2 | 9/2017 | Cohen et al. |
| D800,908 S | 10/2017 | Hariton et al. |
| 9,788,941 B2 | 10/2017 | Hacohen |
| 9,987,132 B1 | 6/2018 | Hariton et al. |
| 10,010,414 B2 | 7/2018 | Cooper et al. |
| 10,076,415 B1 | 9/2018 | Metchik et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,258,471 B2 | 4/2019 | Lutter et al. |

(56) References Cited

U.S. PATENT DOCUMENTS

| | | |
|---|---|---|
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,376,361 B2 | 8/2019 | Gross et al. |
| 10,507,108 B2 | 12/2019 | Delgado et al. |
| 10,507,109 B2 | 12/2019 | Metchik et al. |
| 10,524,792 B2 | 1/2020 | Hernandez et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,646,342 B1 | 5/2020 | Marr et al. |
| 10,813,760 B2 | 10/2020 | Metchik et al. |
| 10,820,998 B2 | 11/2020 | Marr et al. |
| 10,905,554 B2 | 2/2021 | Cao |
| 2001/0021872 A1 | 9/2001 | Bailey et al. |
| 2001/0056295 A1 | 12/2001 | Solem |
| 2002/0013571 A1 | 1/2002 | Goldfarb et al. |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0036791 A1 | 2/2003 | Philipp et al. |
| 2003/0060875 A1 | 3/2003 | Wittens |
| 2003/0069635 A1 | 4/2003 | Cartledge et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0030382 A1 | 2/2004 | St. Goar et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0236354 A1 | 11/2004 | Seguin |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0085900 A1 | 4/2005 | Case et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0203618 A1 | 9/2005 | Sharkawy et al. |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020275 A1 | 1/2006 | Goldfarb et al. |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0047297 A1 | 3/2006 | Case |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Hebert et al. |
| 2006/0135964 A1 | 6/2006 | Vesely |
| 2006/0155357 A1 | 7/2006 | Melsheimer |
| 2006/0178700 A1 | 8/2006 | Quinn |
| 2006/0178740 A1 | 8/2006 | Stacchino et al. |
| 2006/0184203 A1 | 8/2006 | Martin et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0229708 A1 | 10/2006 | Powell et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0282150 A1 | 12/2006 | Olson et al. |
| 2006/0287719 A1 | 12/2006 | Rowe et al. |
| 2007/0016288 A1 | 1/2007 | Gurskis et al. |
| 2007/0027528 A1 | 2/2007 | Agnewl |
| 2007/0027549 A1 | 2/2007 | Godin |
| 2007/0038293 A1 | 2/2007 | St.Goar et al. |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtain |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0239273 A1 | 10/2007 | Allen |
| 2007/0244546 A1 | 10/2007 | Francis |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe |
| 2008/0086204 A1 | 4/2008 | Rankin |
| 2008/0091261 A1 | 4/2008 | Long et al. |

(56) References Cited

U.S. PATENT DOCUMENTS

| | | |
|---|---|---|
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quadri |
| 2009/0319037 A1 | 12/2009 | Rowe et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0324595 A1 | 12/2010 | Linder et al. |
| 2010/0331971 A1 | 12/2010 | Keranen et al. |
| 2011/0004227 A1 | 1/2011 | Goldfarb et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0021985 A1 | 1/2011 | Spargias |
| 2011/0022165 A1 | 1/2011 | Oba et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0066233 A1 | 3/2011 | Thornton et al. |
| 2011/0071626 A1 | 3/2011 | Wright et al. |
| 2011/0077730 A1 | 3/2011 | Fenster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao et al. |
| 2011/0283514 A1 | 11/2011 | Fogarty et al. |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301701 A1 | 12/2011 | Padala et al. |

(56) References Cited

U.S. PATENT DOCUMENTS

| | | |
|---|---|---|
| 2011/0301702 A1 | 12/2011 | Rust et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0000112 A1 | 1/2014 | Braido et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0222142 A1 | 8/2014 | Kovalsky et al. |
| 2014/0222163 A1 | 8/2014 | Xu et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0272734 A1 | 10/2015 | Sheps et al. |

(56) References Cited

U.S. PATENT DOCUMENTS

| | | |
|---|---|---|
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0095700 A1 | 4/2016 | Righini |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford, III et al. |
| 2016/0331526 A1 | 11/2016 | Schweich, Jr. et al. |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0062760 A1 | 3/2017 | Kim |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2017/0239048 A1 | 8/2017 | Goldfarb et al. |
| 2017/0249494 A1 | 8/2017 | Zhang et al. |
| 2017/0333187 A1 | 11/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0125644 A1 | 5/2018 | Conklin |
| 2018/0153689 A1 | 6/2018 | Maimon et al. |
| 2018/0177594 A1 | 6/2018 | Patel et al. |
| 2018/0206983 A1 | 7/2018 | Noe et al. |
| 2018/0250126 A1 | 9/2018 | O'connor et al. |
| 2018/0296336 A1 | 10/2018 | Cooper et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0054335 A1 | 2/2020 | Hernandez et al. |
| 2020/0060818 A1 | 2/2020 | Geist et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0138567 A1 | 5/2020 | Marr et al. |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |

FOREIGN PATENT DOCUMENTS

| | | |
|---|---|---|
| CN | 103974674 | 8/2014 |
| CN | 106486520 A | 3/2017 |
| EP | 1264582 A2 | 12/2002 |
| EP | 1768630 B1 | 4/2007 |
| JP | S53152790 | 12/1978 |
| KR | 20010046894 | 6/2001 |
| WO | 98/43557 A1 | 10/1998 |
| WO | 99/30647 A1 | 6/1999 |
| WO | 00/47139 A1 | 8/2000 |
| WO | 01/62189 A1 | 8/2001 |
| WO | 01/82832 | 11/2001 |
| WO | 01/87190 A2 | 11/2001 |
| WO | 2003/020179 | 3/2003 |
| WO | 03/028558 A2 | 4/2003 |
| WO | 2006/007401 A2 | 1/2006 |
| WO | 2006/054930 A1 | 5/2006 |
| WO | 2006/070372 A2 | 7/2006 |
| WO | 2006/086434 | 8/2006 |
| WO | 2006/089236 A1 | 8/2006 |
| WO | 2006/116558 | 11/2006 |
| WO | 2007/059252 A1 | 5/2007 |
| WO | 2008/013915 A3 | 1/2008 |
| WO | 2008/029296 A2 | 3/2008 |
| WO | 2008/070797 A2 | 6/2008 |
| WO | 2008/103722 A2 | 8/2008 |
| WO | 2009/033469 A1 | 3/2009 |
| WO | 2009/053497 A1 | 4/2009 |
| WO | 2009091509 A1 | 7/2009 |
| WO | 2010006627 A1 | 1/2010 |
| WO | 2010/045297 | 4/2010 |
| WO | 2010/057262 | 5/2010 |
| WO | 2010/073246 A2 | 7/2010 |
| WO | 2010/081033 A1 | 7/2010 |
| WO | 2011/025972 A2 | 3/2011 |
| WO | 2011/069048 A2 | 6/2011 |
| WO | 2011/106137 A1 | 9/2011 |
| WO | 2011/111047 A2 | 9/2011 |
| WO | 2011/137531 A1 | 11/2011 |
| WO | 2011/143263 A2 | 11/2011 |
| WO | 2011/154942 A2 | 12/2011 |
| WO | 2012/011108 A2 | 1/2012 |
| WO | 2012/024428 A2 | 2/2012 |
| WO | 2012/036740 A2 | 3/2012 |
| WO | 2012/048035 A2 | 4/2012 |
| WO | 2012/127309 A1 | 9/2012 |
| WO | 2012/177942 A2 | 12/2012 |
| WO | 2013/021374 | 2/2013 |
| WO | 2013/021374 A2 | 2/2013 |
| WO | 2013/021375 | 2/2013 |
| WO | 2013/021375 A2 | 2/2013 |
| WO | 2013/021384 A1 | 2/2013 |
| WO | 2013059747 A1 | 4/2013 |
| WO | 2013/072496 | 5/2013 |
| WO | 2013/078497 A1 | 6/2013 |
| WO | 2013/128436 A1 | 9/2013 |
| WO | 2013/175468 | 11/2013 |
| WO | 2014/022124 A1 | 2/2014 |
| WO | 2014/076696 | 5/2014 |

(56) References Cited

FOREIGN PATENT DOCUMENTS

| WO | 2014/115149 | | 7/2014 |
|----|-------------|----|--------|
| WO | 2014/145338 | A1 | 9/2014 |
| WO | 2014/164364 | A1 | 10/2014 |
| WO | 2015/173794 | A1 | 11/2015 |
| WO | 2016/016899 | | 2/2016 |
| WO | 2016/093877 | A1 | 6/2016 |
| WO | 2016/125160 | A1 | 8/2016 |
| WO | 2017/223486 | A1 | 12/2017 |
| WO | 2018/025260 | A1 | 2/2018 |
| WO | 2018/025263 | | 2/2018 |
| WO | 2018/029680 | A1 | 2/2018 |
| WO | 2018/039631 | A1 | 3/2018 |
| WO | 2018/106837 | A1 | 6/2018 |
| WO | 2018/112429 | A1 | 6/2018 |
| WO | 2018/118717 | A1 | 6/2018 |
| WO | 2018/131042 | A1 | 7/2018 |
| WO | 2018/131043 | A1 | 7/2018 |
| WO | 2019/026059 | | 2/2019 |
| WO | 2019/030753 | | 2/2019 |
| WO | 2019/077595 | | 4/2019 |
| WO | 2019/116369 | | 6/2019 |
| WO | 2019/138400 | | 7/2019 |
| WO | 2019/195860 | | 10/2019 |
| WO | 2019/202579 | | 10/2019 |
| WO | 2020/058972 | | 3/2020 |
| WO | 2020/167677 | | 8/2020 |

OTHER PUBLICATIONS

An Office Action dated Jun. 18, 2018, which issued during the prosecution of UK Patent Application No. 1800399.6.
An Office Action dated Jun. 6, 2018, which issued during the prosecution of UK Patent Application No. 1720803.4.
An International Search Report and a Written Opinion both dated May 13, 2019, which issued during the prosecution of Applicant's PCT/IL2018/051350.
An International Search Report and a Written Opinion both dated Apr. 5, 2019, which issued during the prosecution of Applicant's PCT/IL2019/050142.
An International Search Report and a Written Opinion both dated Jan. 25, 2019, which issued during the prosecution of Applicant's PCT/IL2018/051122.
An International Search Report and a Written Opinion both dated Dec. 5, 2018, which issued during the prosecution of Applicant's PCT/IL2018/050725.
An International Preliminary Report on Patentability dated Feb. 12, 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Mar. 25, 2019, which issued during the prosecution of European Patent Application No. 14710060.6.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An International Search Report and a Written Opinion both dated Nov. 9, 2018, which issued during the prosecution of Applicant's PCT/IL2018/050869.

U.S. Appl. No. 61/312,412, filed Mar. 10, 2010.
U.S. Appl. No. 13/044,694, filed Mar. 10, 2011, published as 2011/0224785.
U.S. Appl. No. 14/626,267, filed Feb. 19, 2015, published as 2015/0157457 issued as U.S. Pat. No. 9,788,941.
U.S. Appl. No. 15/729,107, filed Oct. 10, 2017, published as 2018/0028311.
Alexander S. Gena, et al; "Replacement of Degenerated Mitral and Aortic Bioprostheses Without Explantation", Ann. Thorac Surg., Jun. 2001; vol. 72, pp. 1509-1514.
Dominique Himbert, MD; "Mital Regurgitation and Stenosis from Bioprosthesis and Annuloplasty Failure: Transcatheter Approaches and Outcomes", TCT 2015.
Josef Jansen, et al; "Detachable Shape-Memory Sewing Ring for Heart Valves", Artif. Organs, vol. 16, No. 3, pp. 294-297, 1992.
Frank Langer, et al; "RING plus STRING: Papillary muscle repositioning as an adjunctive repair technique for ischemic mitral regurgitation", The Journal of Thoracic and Cardiovascular Surgery, vol. 133, No. 1, pp. 247-249; Jan. 2007.
Frank Langer, et al; "RING+STRING Successful Repair Technique for Ischemic Mitral Regurgitation With Severe Leaflet Tethering", Circulation, Sep. 2009; 120[Suppl 1]; pp. S85-S91.
Francesco Maisano; "Valtech Cardiovalve: Novel Design Feature and Clinical Update", TCT 2015.
Giovanni Righini; "Saturn Project a novel solution for transcatheter heart valve replacement specifically designed to address clinical therapeutic needs on mitral valve".
John G. Webb, et al; "Transcatheter Valve-in-Valve Implantation for Failed Bioprosthetic Heart Valves", Circulation, published online Apr. 12, 2010, vol. 121; pp. 1848-1857.
Righini presentation EuroPCR May 2015 (Saturn)—(downloaded from; https://www.pcronline.com/Cases-resourcesimages/Resources/Course-videos-slides/2015/Cardiovascularinnovation-pipeline-Mitral-and-triscuspid-valve-interventions.).
USPTO FOA dated Sep. 12, 2013 in connection with U.S. Appl. No. 13/412,814.
USPTO NOA dated Aug. 18, 2017 in connection with U.S. Appl. No. 14/689,608.
USPTO NOA dated May 10, 2016 in connection with U.S. Appl. No. 14/237,258.
USPTO RR dated Jan. 20, 2016 in connection with U.S. Appl. No. 14/161,921.
USPTO RR dated Aug. 14, 2012 in connection with U.S. Appl. No. 12/961,721.
Extended European Search Report dated Feb. 10, 2017; Appln. 12821522.5.
Extended European Search Report dated Feb. 18, 2015; Appln. 12821522.5.
Extended European Search Report dated Jun. 29, 2017; Appln. 11809374.9.
EPO Communication dated Feb. 10, 2017; Appln. 18821522.5.
Invitation to pay additional fees dated Jan. 2, 2018; PCT/IL2017/050849.
Invitation to pay additional fees dated Sep. 29, 2017; PCT/IL2017/050873.
Invitation to pay additional fees dated Jun. 12, 2014; PCT/IL2014/050087.
IPRP issued Feb. 11, 2014; PCT/IL2012/000292.
IPRP issued Feb. 11, 2014; PCT/IL2012/000293.
IPRP issued Sep. 11, 2012; PCT/IL2011/000231.
IPRP issued Dec. 2, 2013; PCT/IL2011/000582.
International Search Report dated Oct. 13, 2011; PCT/IL11/00231.
International Search Report and Written Opinion dated Feb. 6, 2013; PCT/IL2012/000292.
International Search Report and Written Opinion dated Feb. 6, 2013; PCT/IL2012/00293.
International Search Report and Written Opinion dated Mar. 17, 2014; PCT/IL13/50937.
International Search Report and Written Opinion dated May 30, 2016; PCT/IL2016/050125.
International Search Report and Written Opinion dated Jun. 20, 2018; PCT/IL2018/050024.

(56) References Cited

OTHER PUBLICATIONS

International Search Report and Written Opinion dated Sep. 4, 2014; PCT/IL2014/050087.
International Search Report and Written Opinion dated Oct. 27, 2015; PCT/IL2015/050792.
Internationai Search Report and Written Opinion dated Dec. 5, 2011; PCT/IL11/00582.
Office Action issued by the UK dated Feb. 7, 2017; Appln. GB1613219.3.
U.S. Appl. No. 61/283,819.
U.S. Appl. No. 61/492,449.
U.S. Appl. No. 61/515,372.
U.S. Appl. No. 61/525,281.
U.S. Appl. No. 61/537,276.
U.S. Appl. No. 61/555,160.
U.S. Appl. No. 61/588,892.
U.S. Appl. No. 61/312,412.
USPTO FOA dated Jan. 17, 2018 in connection with U.S. Appl. No. 14/763,004.
USPTO FOA dated Feb. 10, 2014 in connection with U.S. Appl. No. 13/033,852.
USPTO FOA dated Feb. 15, 2013 in connection with U.S. Appl. No. 12/840,463.
USPTO FOA dated Feb. 25, 2016 in connection with U.S. Appl. No. 14/522,987.
USPTO FOA dated Mar. 25, 2015 in connection with U.S. Appl. No. 12/840,463.
USPTO FOA dated Apr. 13, 2016 in connection with U.S. Appl. No. 14/626,267.
USPTO FOA dated May 23, 2014 in connection with U.S. Appl. No. 13/412,814.
USPTO FOA dated Jul. 18, 2013 in connection with U.S. Appl. No. 13/044,694.
USPTO FOA dated Jul. 23, 2013 in connection with U.S. Appl. No. 12/61,721.
USPTO Applicant-Initiated Interview Summary dated Feb. 8, 2018 in connection with U.S. Appl. No. 15/213,791.
USPTO NFOA dated Jan. 5, 2018 in connection with U.S. Appl. No. 15/541,783.
USPTO NFOA dated Jan. 18, 2017 in connection with U.S. Appl. No. 14/626,267.
USPTO NFOA dated Jan. 20, 2016 in connection with U.S. Appl. No. 14/161,921.
USPTO NFOA dated Jan. 21, 2016 in connection with U.S. Appl. No. 14/237,264.
USPTO NFOA dated Feb. 2, 2018 in connection with U.S. Appl. No. 15/329,920.
USPTO NFOA dated Feb. 6, 2013 in connection with U.S. Appl. No. 13/412,814.
USPTO NFOA dated May 15, 2013 in connection with U.S. Appl. No. 12/583,979.
USPTO NFOA dated May 29, 2012 in connection with U.S. Appl. No. 12/840,463.
USPTO NFOA dated Jun. 4, 2014 in connection with U.S. Appl. No. 12/840,463.
USPTO NFOA dated Jun. 17, 2014 in connection with U.S. Appl. No. 12/961,721.
USPTO NFOA dated Jun. 28, 2018 in connection with U.S. Appl. No. 29,635,658.
USPTO NFOA dated Jun. 28, 2018 in connection with U.S. Appl. No. 29/635,661.
USPTO NFOA dated Jun. 30, 2015 in connection with U.S. Appl. No. 14/522,987.
USPTO NFOA dated Jul. 1, 2016 in connection with U.S. Appl. No. 14/161,921.
USPTO NFOA dated Jul. 2, 2014 in connection with U.S. Appl. No. 13/811,308.
USPTO NFOA dated Jul. 3, 2014 in connection with U.S. Appl. No. 13/033,852.
USPTO NFOA dated Jul. 26, 2018 in connection with U.S. Appl. No. 15/872,501.
USPTO NFOA dated Aug. 2, 2013 in connection with U.S. Appl. No. 13/033,852.
USPTO NFOA dated Aug. 6, 2018 in connection with U.S. Appl. No. 15/729,107.
USPTO NFOA dated Aug. 9, 2018 in connection with U.S. Appl. No. 15/899,858.
USPTO NFOA dated Aug. 9, 2018 in connection with U.S. Appl. No. 15/902,403.
USPTO NFOA dated Aug. 14, 2012 in connection with U.S. Appl. No. 12/961,721.
USPTO NFOA dated Sep. 12, 2013 in connection with U.S. Appl. No. 13/412,814.
USPTO NFOA dated Sep. 19, 2014 in connection with U.S. Appl. No. 13/044,694.
USPTO NFOA dated Oct. 23, 2017 in connection with U.S. Appl. No. 14/763,004.
USPTO NFOA dated Nov. 8, 2013 in connection with U.S. Appl. No. 12/840,463.
USPTO NFOA dated Nov. 23, 2012 in connection with U.S. Appl. No. 13/033,852.
USPTO NFOA dated Nov. 27, 2015 in connection with U.S. Appl. No. 14/626,267.
USPTO NFOA dated Nov. 28, 2012 in connection with U.S. Appl. No. 12/961,721.
USPTO NFOA dated Dec. 7, 2017 in connection with U.S. Appl. No. 15/213,791.
USPTO NFOA dated Dec. 10, 2015 in connection with U.S. Appl. No. 14/237,258.
USPTO NFOA dated Dec. 31, 2012 in connection with U.S. Appl. No. 13/044,694.
USPTO NOA dated Feb. 11, 2015 in connection with U.S. Appl. No. 13/033,852.
USPTO NOA dated Mar. 10, 2015 in connection with U.S. Appl. No. 13/811,308.
USPTO NOA dated Apr. 8, 2016 in connection with U.S. Appl. No. 14/237,258.
USPTO NOA dated Apr. 20, 2018 in connection with U.S. Appl. No. 15/878,206.
USPTO NOA dated May 5, 2015 in connection with U.S. Appl. No. 12/840,463.
USPTO NOA dated May 22, 2017 in connection with U.S. Appl. No. 14/689,608.
USPTO NOA dated Jun. 20, 2017 in connection with U.S. Appl. No. 14/626,267.
USPTO NOA dated Aug. 15, 2014 in connection with U.S. Appl. No. 13/412,814.
USPTO Notice of Abandonment dated Jul. 9, 2015 in connection with U.S. Appl. No. 13/044,694.
USPTO RR dated Feb. 3, 2014 in connection with U.S. Appl. No. 13/811,308.
USPTO RR dated Apr. 21, 2017 in connection with U.S. Appl. No. 15/213,791.
USPTO RR dated May 4, 2018 in connection with U.S. Appl. No. 15/872,501.
USPTO RR dated Jun. 17, 2014 in connection with U.S. Appl. No. 12/961,721.
USPTO RR dated Jul. 2, 2012 in connection with U.S. Appl. No. 13/033,852.
USPTO RR dated Aug. 13, 2012 in connection with U.S. Appl. No. 13/044,694.
USPTO RR dated Aug. 28, 2015 in connection with U.S. Appl. No. 14/237,264.
USPTO RR dated Sep. 26, 2016 in connection with U.S. Appl. No. 14/763,004.
USPTO RR dated Nov. 6, 2015 in connection with U.S. Appl. No. 14/626,267.
USPTO RR dated Nov. 28, 2012 in connection with U.S. Appl. No. 12/961,721.
USPTO Supplemental NOA dated May 10, 2016 in connection with U.S. Appl. No. 14/237,258.

(56) References Cited

OTHER PUBLICATIONS

USPTO Supplemental NOA dated May 20, 2016 in connection with U.S. Appl. No. 14/237,258.
USPTO Supplemental NOA dated Jul. 6, 2017 in connection with U.S. Appl. No. 14/689,608.
USPTO NFOA dated Feb. 7, 2017 in connection with U.S. Appl. No. 14/689,608.
USPTO NFOA dated Feb. 7, 2018 in connection with U.S. Appl. No. 15/197,069.
USPTO NFOA dated Apr. 20, 2018 in connection with U.S. Appl. No. 15/886,517.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
An Office Action dated Aug. 1, 2019, which issued during the prosecution of U.S. Appl. No. 15/668,559.
An Office Action dated Aug. 16, 2019, which issued during the prosecution of U.S. Appl. No. 15/668,659.
An Office Action dated Jun. 19, 2019, which issued during the prosecution of U.S. Appl. No. 15/682,789.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Nov. 1, 2019, which issued during the prosecution of U.S. Appl. No. 15/872,501.
Notice of Allowance dated May 7, 2020, which issued during the prosecution of U.S. Appl. No. 16/637,166.
Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dg=%20%22Edwards%20SAPIEN%22&lr&pg=PA20#v=onepage&q=%22Edwards%20SAPIEN%22&f=false ; Downloaded on Jun. 18, 2020.
An International Search Report and a Written Opinion both dated Jun. 24, 2020, which issued during the prosecution of Applicant's PCT/IL2019/051398.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
Notice of Allowance dated Jul. 29, 2020, which issued during the prosecution of U.S. Appl. No. 16/132,937.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Aug. 7, 2020, which issued during the prosecution of U.S. Appl. No. 15/668,659.
Tchetche, D. and Nicolas M. Van Mieghem: "New-generation TAVI devices: description and specifications" EuroIntervention, 2014, No. 10:U90-U100.
Symetis S.A.: "ACURATE neo™ Aortic Bioprosthesis for Implantation using the Acurate neo™ TA Transapical Delivery System in Patients with Severe Aortic Stenosis," Clinical Investigation Plan, Protocol No. 2015-01, Vs. No. 2, 2015:1-76.
Notice of Allowance dated Sep. 10, 2020, which issued during the prosecution of U.S. Appl. No. 15/600,190.
An Office Action dated Feb. 2, 2021, which issued during the prosecution of U.S. Appl. No. 16/811,732.
An Office Action dated Dec. 24, 2020, which issued during the prosecution of U.S. Appl. No. 16/144,054.
An Office Action dated Jan. 13, 2021 which issued during the prosecution of European Patent Application No. 15751089.2.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
U.S. Appl. No. 60/128,690, filed Apr. 9, 1999.
Batista, Randas JV, et al. "Partial left ventriculectomy to treat end-stage heart disease." The Annals of thoracic surgery 64.3 (1997): 634-638.
Beall Jr, Arthur C., et al. "Clinical experience with a dacron velour-covered teflon-disc mitral-valve prosthesis." The Annals of thoracic surgery 5.5 (1968): 402-410.
Mitral Valve Academic Research Consortium. "Clinical Trial Design Principles and Endpoint Definitions for Transcatheter Mitral Valve Repair and Replacement: Part 1: Clinical Trial Design Principles A Consensus Document from the Mitral Valve Academic Research Consortium." Journal of the American College of Cardiology 66.3 (2015): 278-307.
U.S. Appl. No. 60/613,867, filed Sep. 27, 2004.
Kalbacher, D., et al. "1000 MitraClip™ procedures: Lessons learnt from the largest single-centre experience worldwide." (2019): 3137-3139.
Declaration of Dr. Ivan Vesely, Ph.D. In Support of Petition for Inter Partes Review of U.S. Pat. No. 10,226,341—dated Dec. 17, 2020.
Declaration of Ivan Vesely, Ph.D., in Support of Petition for Inter Partesreview of U.S. Pat. No. 7,563,267—dated May 29, 2019.
An Office Action together with an English summary dated Mar. 3, 2021, which issued during the prosecution of Chinese Patent Application No. 201780047391.4.
An International Preliminary Report on Patentability dated Oct. 20, 2020, which issued during the prosecution of Applicant's PCT/IL2019/050142.
An Office Action dated Oct. 5, 2020, which issued during the prosecution of Canadian Patent Application No. 2,973,940.
Notice of Allowance dated Nov. 19, 2020, which issued during the prosecution of U.S. Appl. No. 16/318,025.
An Office Action dated Sep. 24, 2020, which issued during the prosecution of U.S. Appl. No. 16/811,732.
An Office Action summarized English translation and Search Report dated Nov. 25, 2020, which issued during the prosecution of Chinese Patent Application No. 201910449820.1.

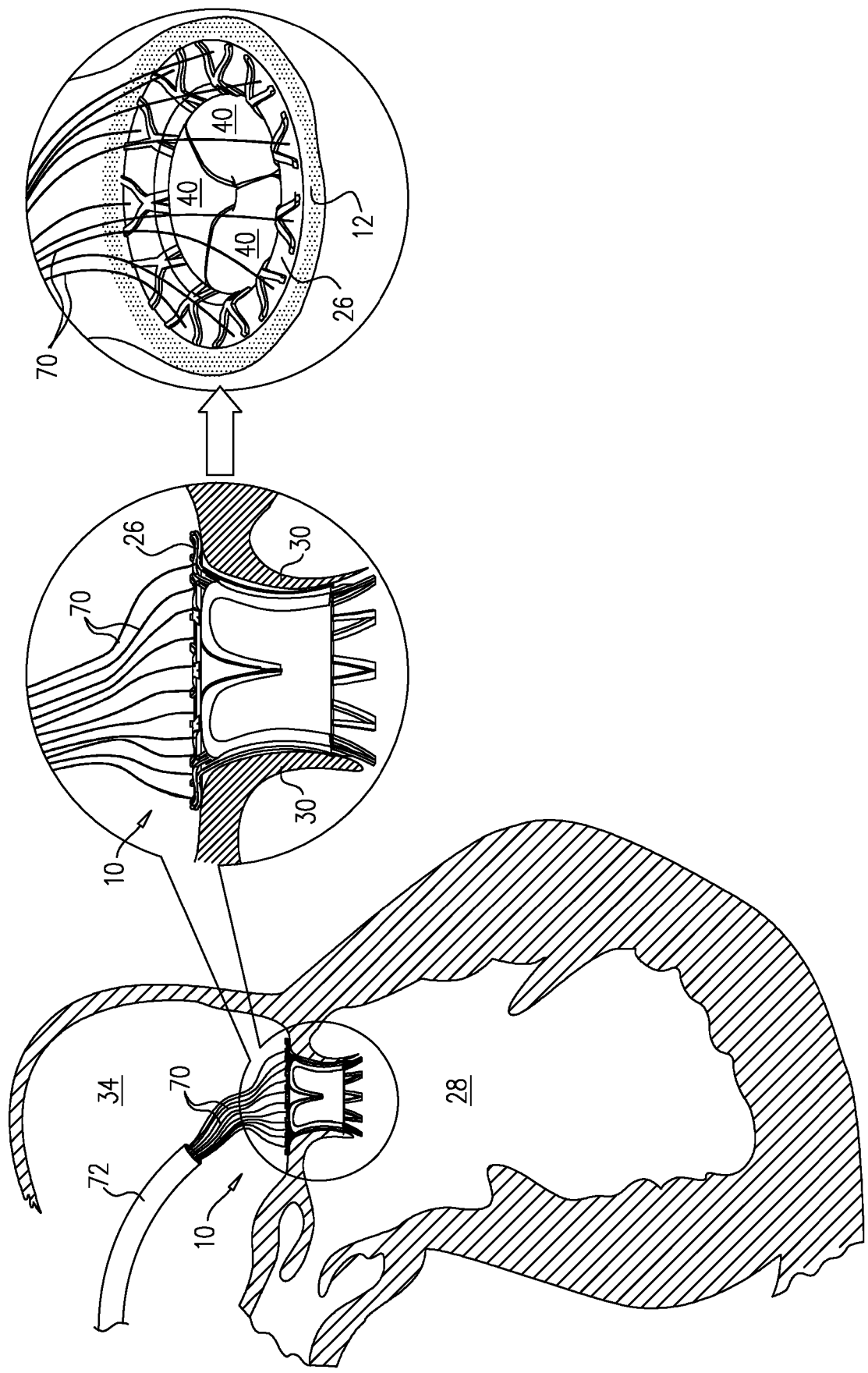

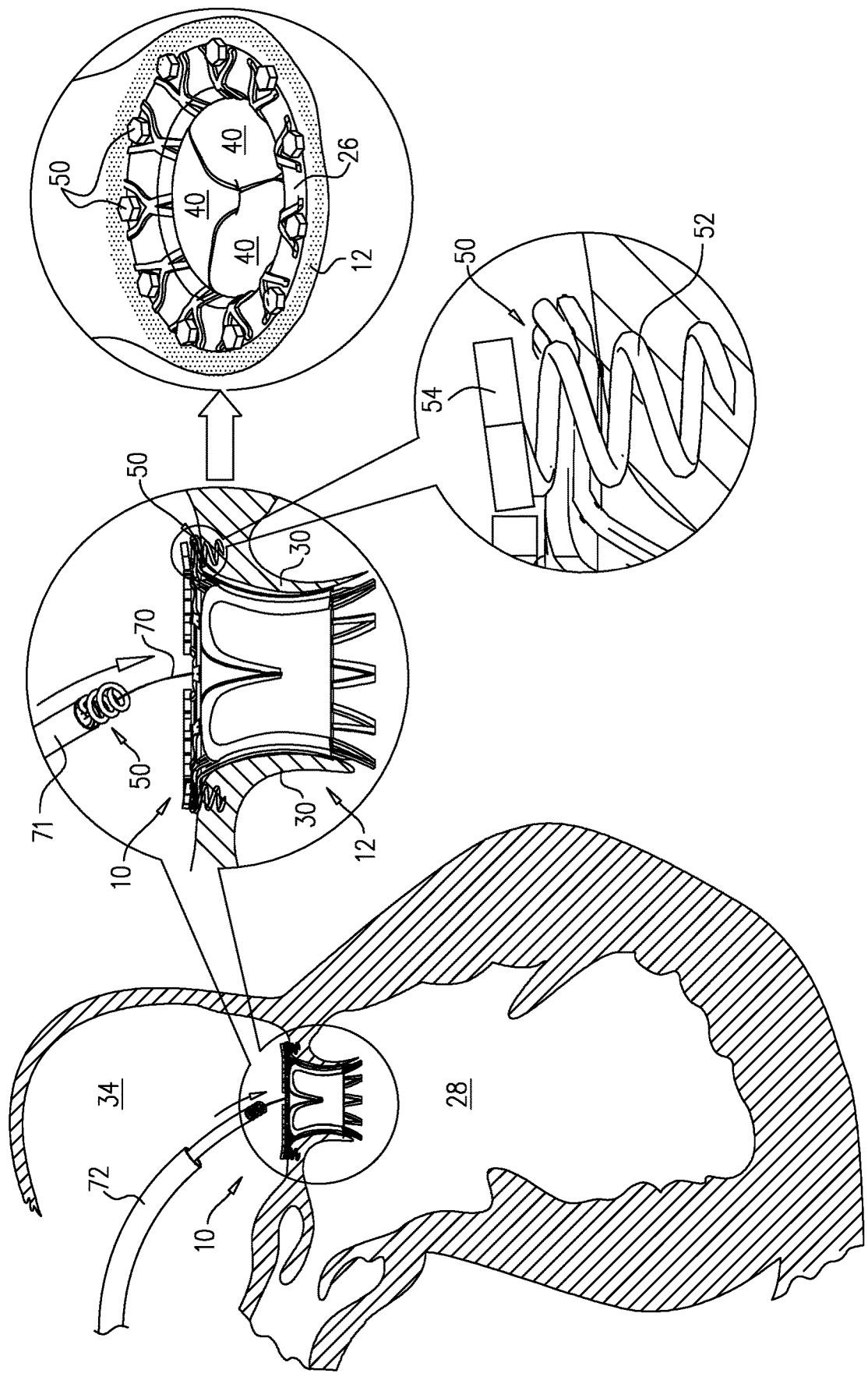

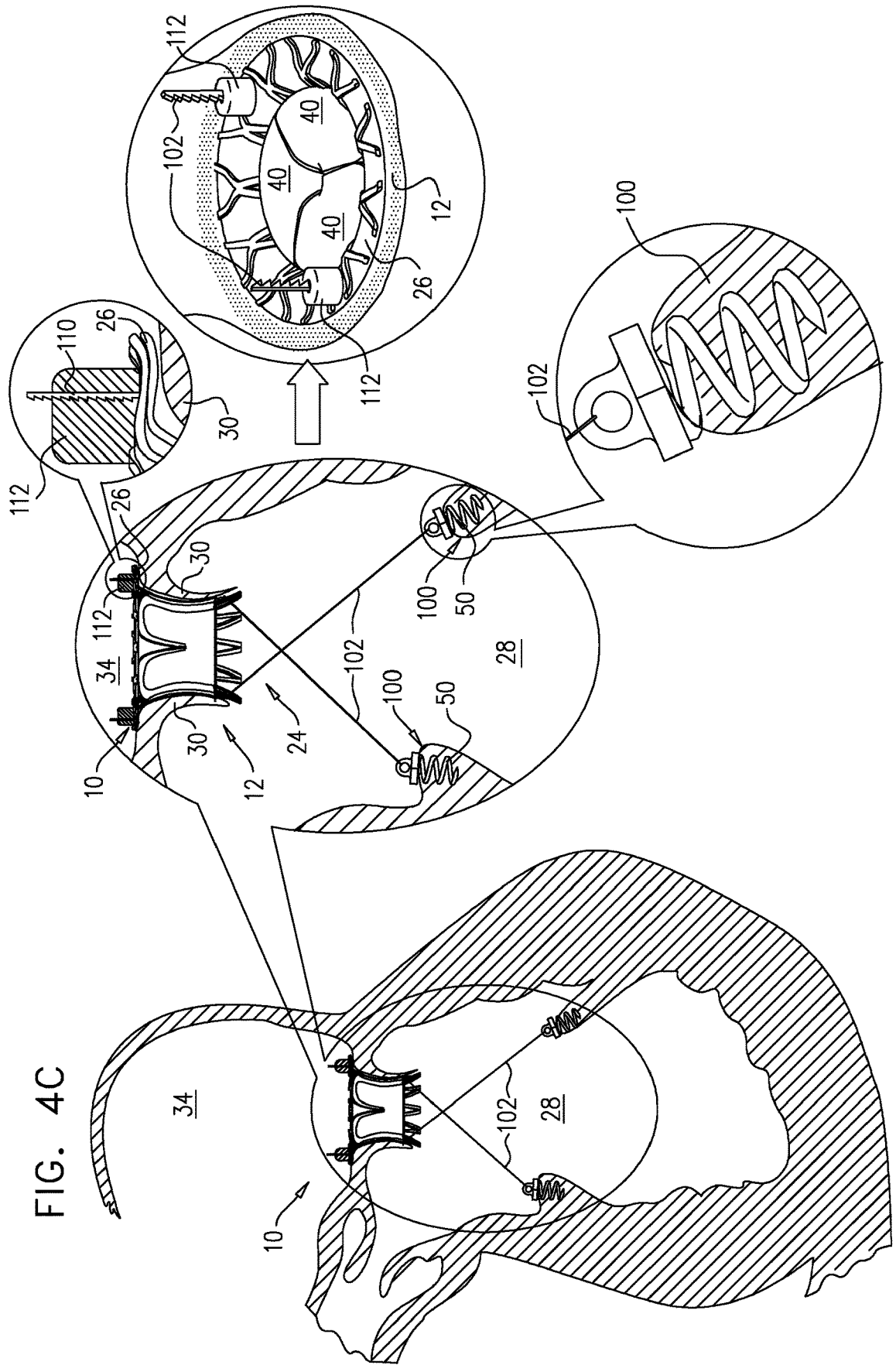

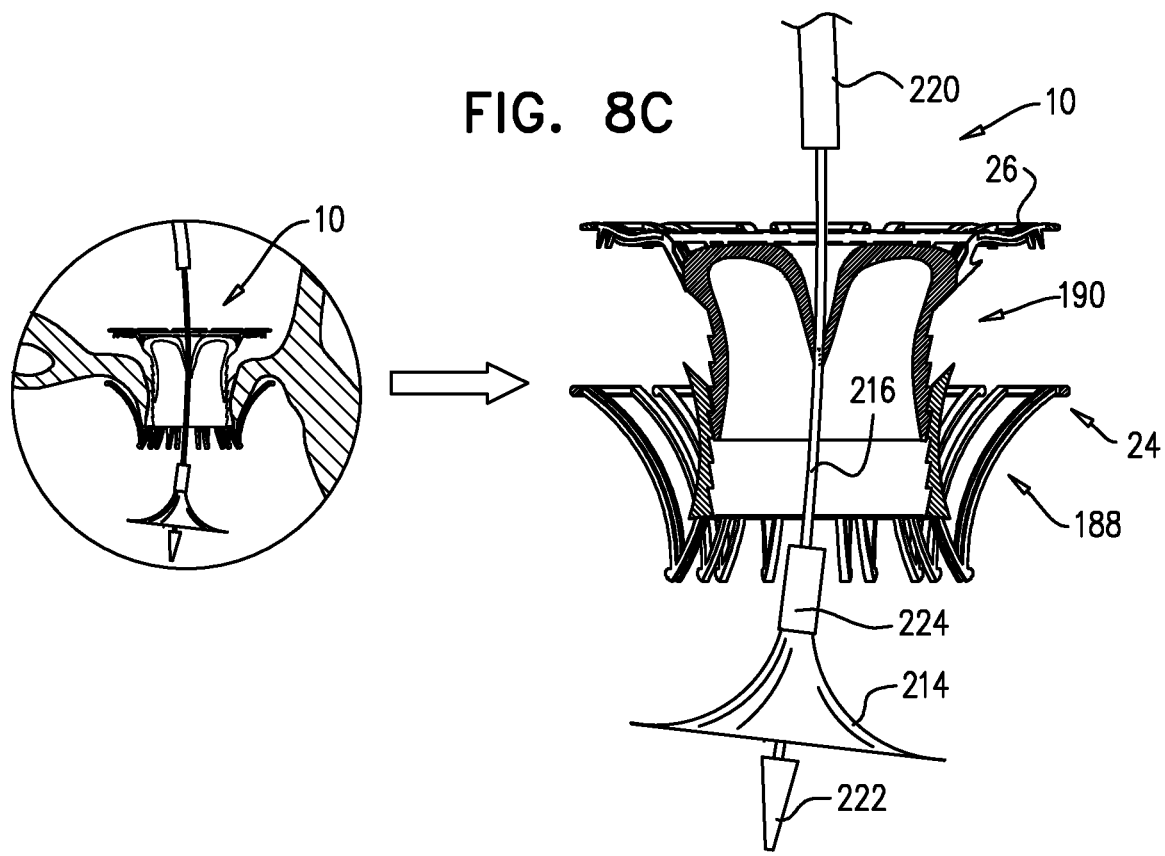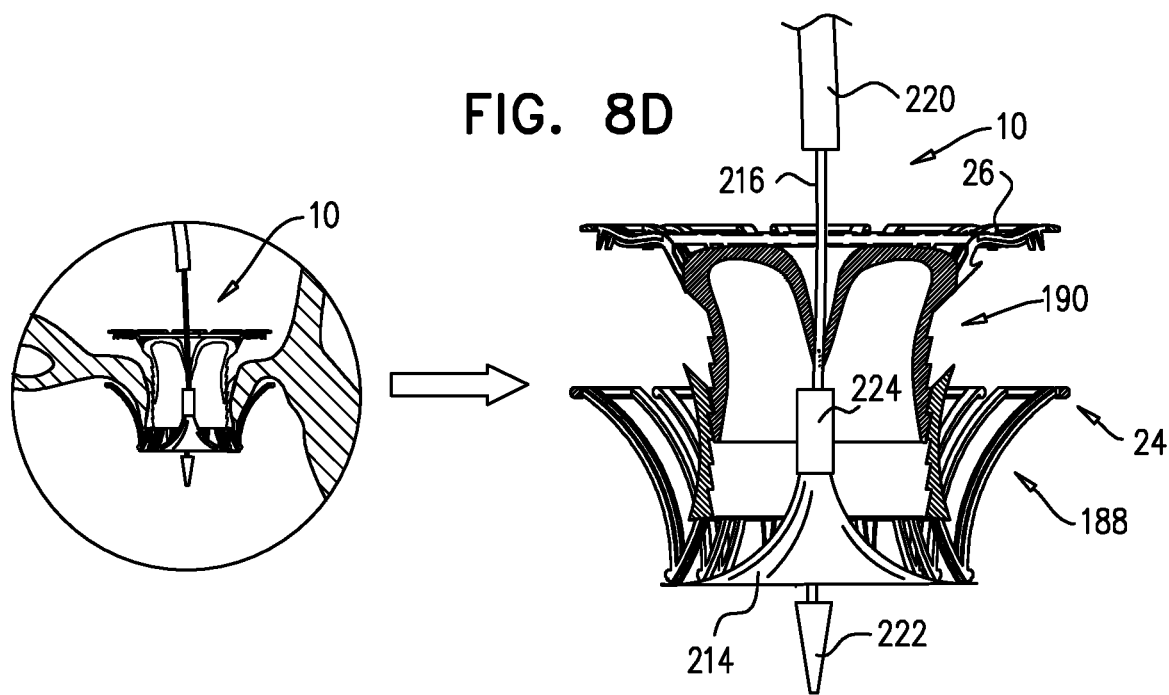

AXIALLY-SHORTENING PROSTHETIC VALVE

CROSS-REFERENCE TO RELATED APPLICATIONS

The present application is a Continuation of U.S. patent application Ser. No. 15/729,107 to HaCohen, entitled "Techniques for securing prosthetic valves using helical anchors," filed Oct. 10, 2017, which published as US 2018/0028311, and which is a Continuation of U.S. patent application Ser. No. 14/626,267 to HaCohen, entitled "Axially-shortening prosthetic valve," filed Feb. 19, 2015 (now U.S. Pat. No. 9,788,941), which is a Divisional of U.S. patent application Ser. No. 13/044,694 to HaCohen, entitled "Prosthetic mitral valve with tissue anchors," filed Mar. 10, 2011 (now abandoned), and which claims priority from U.S. Provisional Application 61/312,412, filed Mar. 10, 2010, entitled, "Prosthetic mitral valve with tissue anchors," which is assigned to the assignee of the present application and is incorporated herein by reference.

The present application is related to international patent application PCT IL2011/000231 entitled "Prosthetic mitral valve with tissue anchors," filed Mar. 10, 2011, which published as WO 2011/111047, which is assigned to the assignee of the present application and is incorporated herein by reference.

FIELD OF EMBODIMENTS OF THE INVENTION

Embodiments of the present invention relate in general to valve replacement. More specifically, embodiments of the present invention relate to prosthetic valves for minimally-invasive replacement of an atrioventricular valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF APPLICATIONS

For some applications of the present invention, a collapsible prosthetic valve is configured for implantation in and/or at least partial replacement of a native atrioventricular valve of a patient, such as a native mitral valve or a native tricuspid valve. The prosthetic valve is configured to assume a collapsed state for minimally-invasive delivery to the diseased native valve, such as by percutaneous or transluminal delivery using one or more catheters. The prosthetic valve comprises a collapsible flexible support, which is at least partially covered by a covering. The prosthetic valve is shaped so as to define a downstream skirt and an upstream annular skirt. The downstream skirt is configured to be placed at the native valve, such that the downstream skirt passes through the orifice of the native valve and extends towards, and, typically partially into, a ventricle. The downstream skirt typically pushes aside and presses against the native leaflets of the native valve, which are typically left in place during and after implantation of the prosthetic valve. The upstream annular skirt is configured to be placed around a native annulus of the native valve, and to extend at least partially into an atrium such that annular skirt rests against the native annulus.

There is therefore provided, in accordance with some applications of the present invention, apparatus including a prosthetic atrioventricular valve for coupling to a native atrioventricular valve, the prosthetic valve including:

a support frame;

a covering, which at least partially covers the support frame, the support frame and the covering being shaped so as to define a downstream skirt;

a plurality of prosthetic leaflets, coupled to at least one element selected from the group consisting of: the support frame and the covering; and an elongated anchoring member, configured to be positioned around the downstream skirt in a subvalvular space, such that the anchoring member presses native leaflets of the native valve against the downstream skirt, thereby anchoring the prosthetic valve to the native valve.

For some applications, the elongated anchoring member is configured to be positioned completely around the downstream skirt.

For some applications, the prosthetic valve further includes a contracting housing shaped so as to define a channel therethrough, a first end of the anchoring member is fixed to the contracting housing, and a second end of the anchoring member passes through the channel.

For some applications, the prosthetic valve is configured to assume collapsed and expanded states.

There is further provided, in accordance with some applications of the present invention, apparatus including a prosthetic atrioventricular valve for coupling to a native atrioventricular valve, the prosthetic valve including:

a support frame;

a covering, which at least partially covers the support frame, the support frame and the covering being shaped so as to define a downstream skirt;

a plurality of prosthetic leaflets, coupled to at least one element selected from the group consisting of: the support frame and the covering; and a plurality of subvalvular anchoring elements, coupled to the downstream skirt, and configured to anchor the prosthetic valve to the native valve by piercing native leaflets of the native valve, passing through to a subvalvular space, and applying a force against the ventricular surface of the native leaflets.

For some applications, the prosthetic valve is configured to assume collapsed and expanded states.

For some applications, each of the tissue coupling elements is shaped as an element selected from the group consisting of: a hollow needle, a solid needle, a rod, and a rectangular plate.

For some applications, the tissue coupling elements are configured to assume a curved shape when in resting states.

For some applications, the tissue coupling elements are shaped so as to define respective barbs.

For some applications, the tissue coupling elements include needles.

For some applications, the needles are configured to assume curved shapes when in resting states.

For some applications, the needles are shaped so as to define respective lumens, and the apparatus further includes an implantation tool, which includes a plurality of rigid rods initially positioned in the lumens, respectively, so as to at least partially straighten the needles.

For some applications, the needles include a shape memory alloy.

There is additionally provided, in accordance with some applications of the present invention, apparatus including a prosthetic atrioventricular valve for coupling at a native valve, the prosthetic valve including:

a support frame;

a covering, which at least partially covers the support frame, the support frame and the covering being shaped so as to define an upstream annular skirt;

a plurality of prosthetic leaflets, coupled to at least one element selected from the group consisting of: the support frame and the covering;

a plurality of longitudinal members, coupled to the upstream annular skirt at respective sites; and a plurality of tissue anchors, configured to be guided along the longitudinal members, respectively, and to couple the upstream annular skirt to cardiac tissue in a vicinity of the native valve.

For some applications, the prosthetic valve is configured to assume collapsed and expanded states.

For some applications, the tissue anchors are configured to pass over the respective longitudinal members.

For some applications, the longitudinal members include respective wires, and the tissue anchors are configured to be guided along the respective wires.

For some applications, each of the tissue anchors includes a coupling element that is shaped so as to define a shape selected from the group consisting of: a helix, a spiral, a corkscrew, and a screw shaft.

For some applications, the longitudinal members are removably coupled to the upstream annular skirt at the respective sites.

For some applications, the prosthetic valve further includes a downstream skirt.

For some applications, the prosthetic valve further includes a ventricular anchoring assembly, which includes:

a ventricular tissue anchor; and a ventricular longitudinal member, a first end of which is coupled to the support structure, and a second end of which is coupled to the ventricular tissue anchor.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define a downstream skirt, (c) a plurality of prosthetic leaflets, coupled to at least one element selected from the group consisting of: the support frame and the covering, and (d) an elongated anchoring member;

placing the prosthetic valve at a native valve of a subject, such that the downstream skirt passes through an orifice of the native valve toward a ventricle of the subject; and anchoring the prosthetic valve to the native valve by positioning the elongated anchoring member around the downstream skirt in a subvalvular space, such that the anchoring member presses native leaflets of the native valve against the downstream skirt.

For some applications, the prosthetic valve further includes a contracting housing shaped so as to define a channel therethrough, a first end of the anchoring member being fixed to the contracting housing, and a second end of the anchoring member passing through the channel, and anchoring further includes pulling on the second end of the anchoring member to tighten the anchoring member around the native leaflets.

For some applications, placing the prosthetic valve includes delivering the prosthetic valve to the native valve while the prosthetic valve is in a collapsed state in a catheter, and deploying the prosthetic valve from the catheter such that prosthetic valve assumes an expanded state.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define a downstream skirt, (c) a plurality of prosthetic leaflets, coupled to at least one element selected from the group consisting of: the support frame and the covering, and (d) a plurality of subvalvular anchoring elements, coupled to the downstream skirt;

placing the prosthetic valve at a native valve of a subject, such that the downstream skirt passes through an orifice of the native valve toward a ventricle of the subject; and anchoring the prosthetic valve to the native valve by causing the subvalvular anchoring elements to pierce native leaflets of the native valve, pass through to a subvalvular space, and apply a force against the ventricular surface of the native leaflets.

For some applications, placing the prosthetic valve includes delivering the prosthetic valve to the native valve while the prosthetic valve is in a collapsed state in a catheter, and deploying the prosthetic valve from the catheter such that the prosthetic valve assumes an expanded state.

For some applications, placing includes placing the prosthetic valve such that the downstream skirt pushes aside and presses against the native leaflets.

For some applications, the needles are shaped so as to define respective lumens, and anchoring includes causing the subvalvular anchoring elements to pierce the native leaflets while a rigid rods are initially positioned in the lumens, respectively, so as to at least partially straighten the needles, and subsequently withdrawing the rods from the lumens.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define an upstream annular skirt, (c) a plurality of prosthetic leaflets, coupled to at least one element selected from the group consisting of: the support frame and the covering, and (d) a plurality of longitudinal members, coupled to the upstream annular skirt at respective sites;

placing the prosthetic valve at a native valve of a subject, such that the upstream annular skirt rests against a native annulus of the native valve, and the longitudinal members extend into an atrium of the subject;

guiding a plurality of tissue anchors along the longitudinal members, respectively; and using the anchors, coupling the upstream annular skirt to cardiac tissue in a vicinity of the native valve.

For some applications, the method further includes decoupling the elongated members from the upstream annular skirt.

For some applications, the method further includes, after placing the prosthetic valve at the native valve and before coupling the upstream annular skirt to the cardiac tissue using the tissue anchors, temporarily anchoring the prosthetic valve to a ventricular wall of the subject using one or more ventricular cords.

For some applications, placing the prosthetic valve includes delivering the prosthetic valve to the native valve while the prosthetic valve is in a collapsed state in a catheter, and deploying the prosthetic valve from the catheter such that the prosthetic valve assumes an expanded state.

For some applications, placing the prosthetic valve includes placing the prosthetic valve at the native valve such that the longitudinal members pass through the catheter.

For some applications, the prosthetic valve further includes a downstream skirt, and placing includes placing the prosthetic valve at the native valve such the downstream skirt passes through an orifice of the native valve toward a ventricle of the subject.

For some applications, placing includes placing the prosthetic valve such that the downstream skirt pushes aside and presses against native leaflets of the native valve.

The present invention will be more fully understood from the following detailed description of applications thereof, taken together with the drawings, in which:

BRIEF DESCRIPTION OF THE DRAWINGS

FIGS. 2A-B are schematic illustrations of a technique for anchoring the prosthetic valve of FIG. 1 at a native valve, in accordance with an application of the present invention;

FIGS. 4A-C are schematic illustrations of yet another technique for anchoring the prosthetic valve of FIG. 1 at the native valve, in accordance with respective applications of the present invention;

FIGS. 8A-G are schematic illustrations of a valve contraction tool and a procedure for the use thereof, in accordance with an application of the present invention.

DETAILED DESCRIPTION OF APPLICATIONS

Figure 1:
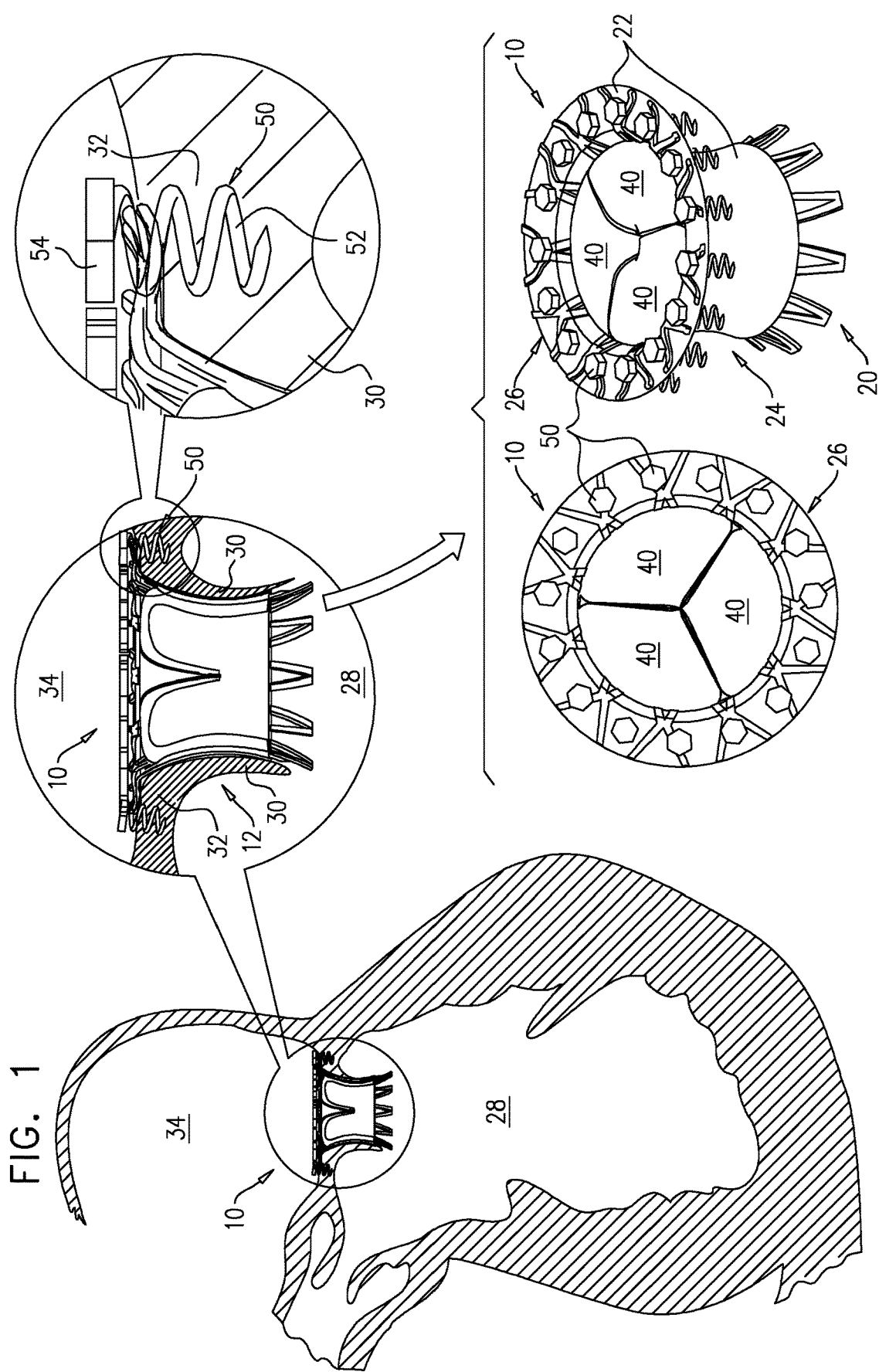
FIG. 1 is a schematic illustration of a collapsible prosthetic valve, in accordance with an application of the present invention.

FIG. 1 is a schematic illustration of a collapsible prosthetic valve 10, in accordance with an application of the present invention. Prosthetic valve 10 is configured for implantation in and/or at least partial replacement of a native atrioventricular valve 12 of a patient, such as a native mitral valve or a native tricuspid valve. The prosthetic valve is typically configured to assume a collapsed state for minimally-invasive delivery to the diseased native valve, such as by percutaneous or transluminal delivery using one or more catheters. FIG. 1 and the other figures show the prosthetic valve in an expanded state after delivery to the native valve.

Prosthetic valve 10 comprises a collapsible flexible support frame 20, which is at least partially covered by a covering 22. The prosthetic valve is shaped so as to define a downstream skirt 24 and an upstream annular skirt 26. The downstream skirt is configured to be placed at native valve 12, such that the downstream skirt passes through the orifice of the native valve and extends towards, and, typically partially into, a ventricle 28. The downstream skirt typically pushes aside and presses against native leaflets 30 of native valve 12, which are typically left in place during and after implantation of the prosthetic valve. The upstream annular skirt is configured to be placed around a native annulus 32 of the native valve, and to extend at least partially into an atrium 34 such that annular skirt rests against the native annulus. The annular skirt is typically too large to pass through the annulus, and may, for example, have an outer diameter of between 30 and 60 mm.

For some applications, collapsible support frame 20 comprises a stent, which comprises a plurality of struts. The struts may comprise, for example, a metal such as Nitinol or stainless steel. For some applications, covering 22 comprises a fabric, such as a woven fabric, e.g., Dacron. Covering 22 is typically configured to cover at least a portion of downstream skirt 24, and at least a portion of upstream annular skirt 26, such as the entire annular skirt (as shown in FIG. 1). The covering may comprise a single piece, or a plurality of pieces sewn together.

Prosthetic valve 10 further comprises a plurality of valve leaflets 40, which may be artificial or tissue-based. The leaflets are typically coupled to an inner surface of the valve prosthesis, such as near the junction between the downstream and upstream skirts 24 and 26. The leaflets are coupled, e.g., sewn, to frame 20 and/or covering 22. For applications in which the prosthetic valve is configured to be implanted at the native mitral valve, the prosthetic valve typically comprises three leaflets 40, such as shown in FIG. 1.

For some applications, such as shown in FIG. 1, prosthetic valve 10 comprises a plurality of tissue anchors 50 for coupling the prosthetic valve to native valve 12, such as the mitral valve. The anchors are typically distributed approximately evenly around upstream annular skirt 26, and couple the upstream skirt to native annulus 32. Typically, each of anchors 50 comprises a tissue-coupling element 52 coupled to a base 54. Tissue-coupling element 52 is configured to pass through upstream annular skirt 26 and penetrate the tissue of the native annulus, and may, for example, be shaped as a corkscrew, spiral, helix, or screw shaft. Base 54 is configured to be too large to pass through the upstream annular skirt. The tissue-coupling element is advanced into the tissue, such as by rotation, until the base comes in contact with and is held tightly against the upstream side of the upstream annular skirt, thus creating a seal between the upstream skirt and the native annulus. For some applications, prosthetic valve 10 comprises between 5 and 20 anchors, such as between 10 and 15 anchors. e.g., 15 anchors. It is noted that, unlike in some prior techniques for coupling prosthetic valves to native valve sites, sutures are typically not used for coupling prosthetic valve 10 to the native valve site.

Reference is now made to FIGS. 2A-B, which are schematic illustrations of a technique for anchoring prosthetic valve 10 at native valve 12, in accordance with an application of the present invention. In this application, prosthetic valve 10 is at least initially coupled to a plurality of flexible elongated members 70, such as wires, cords, or sutures. Elongated members 70 are typically removably coupled to upstream annular skirt 26 at respective sites at which respective anchors 50 subsequently pass through the skirt.

As shown in FIG. 2A, during an implantation procedure, the surgeon places prosthetic valve 10 at a desired location at native valve 12. Elongated members 70 extend into atrium 34, and typically pass through a catheter 72 used to perform the implantation procedure, optionally the same catheter through which prosthetic valve 10 is deployed into the atrium. Optionally, the prosthetic valve is temporarily held in place using the anchoring techniques described hereinbelow with reference to FIGS. 4A-C (or permanently held in place using such anchoring, in combination with the anchoring described hereinbelow with reference to FIG. 2B). For example, the prosthetic valve may be temporarily anchored to the ventricular wall, such as to the apex or one or more papillary muscles, using one or more ventricular cords, as described hereinbelow.

Subsequently, as shown in FIG. 2B, each of anchors 50 is guided along (e.g., passed over, or alongside) a respective one of elongated members 70, until the anchor reaches upstream annular skirt 26. The anchor is coupled to cardiac tissue, such as by using a rotation tool 71 that is separately passed over each of elongated members 70. Typically, the elongated member is then decoupled from upstream annular skirt 26. For example, a cutting tool may be used to decouple the elongated member from the skirt; the cutting tool may be passed through catheter 72, and/or guided along the elongated member. Alternatively, the elongated member may be looped through the skirt, such that both ends of the elongated member remain outside of the patient's body. The surgeon decouples the elongated member from the skirt by releasing one end of the elongated member and pulling on the other end, until the elongated member is drawn from the skirt. Alternatively, the elongated member is cut at some distance from upstream annular skirt 26, such that a portion of the elongated member remains coupled to the upstream annular skirt. These steps are repeated for each of the anchors and elongated members.

These techniques enable the surgeon to readily bring the anchors to the appropriate sites of the upstream annular skirt, without the need for excessive imaging, such as fluoroscopy.

Figure 3A:
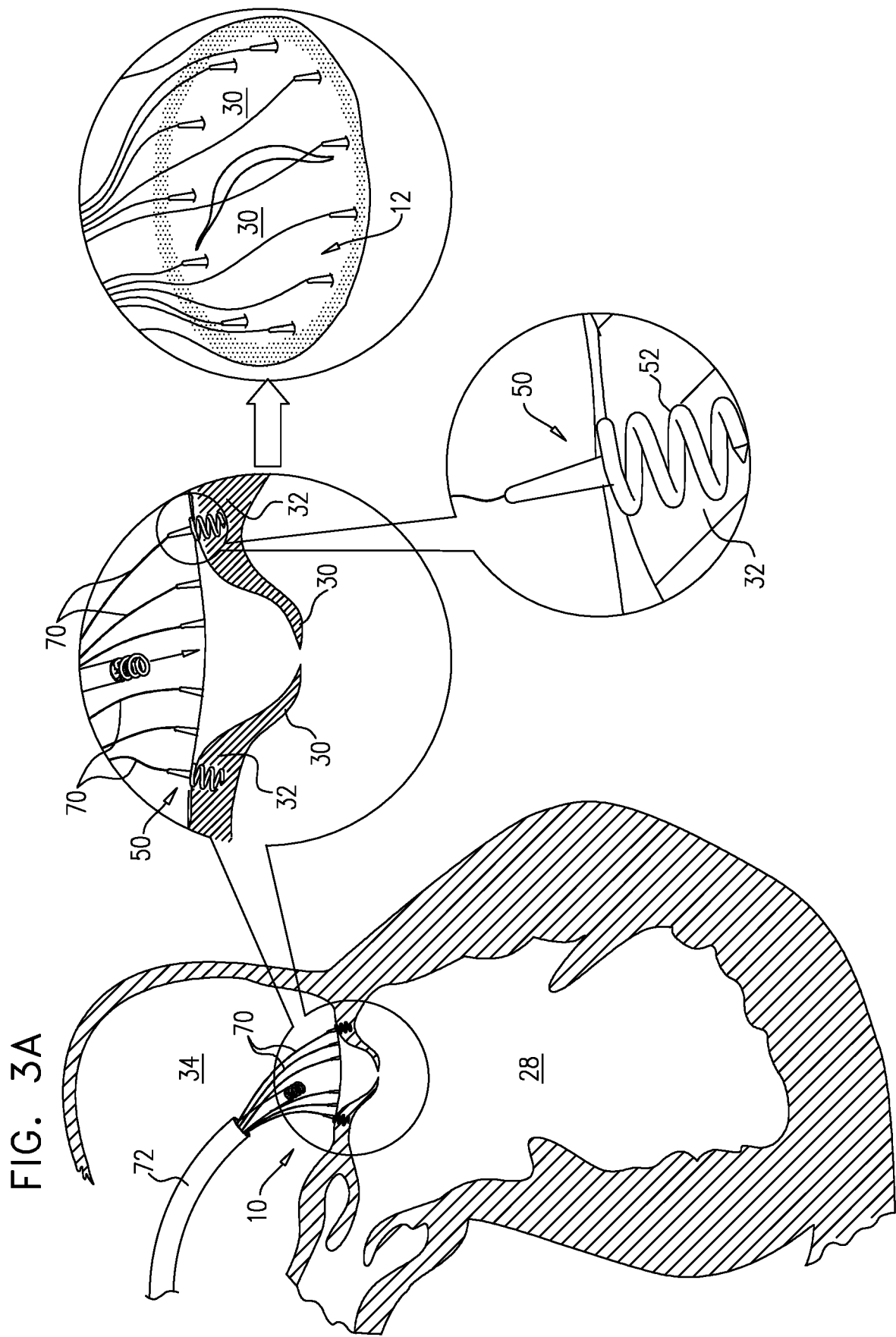
FIGS. 3A-B are schematic illustrations of another technique for anchoring the prosthetic valve of FIG. 1 at the native valve, in accordance with an application of the present invention.
Figure 3B:
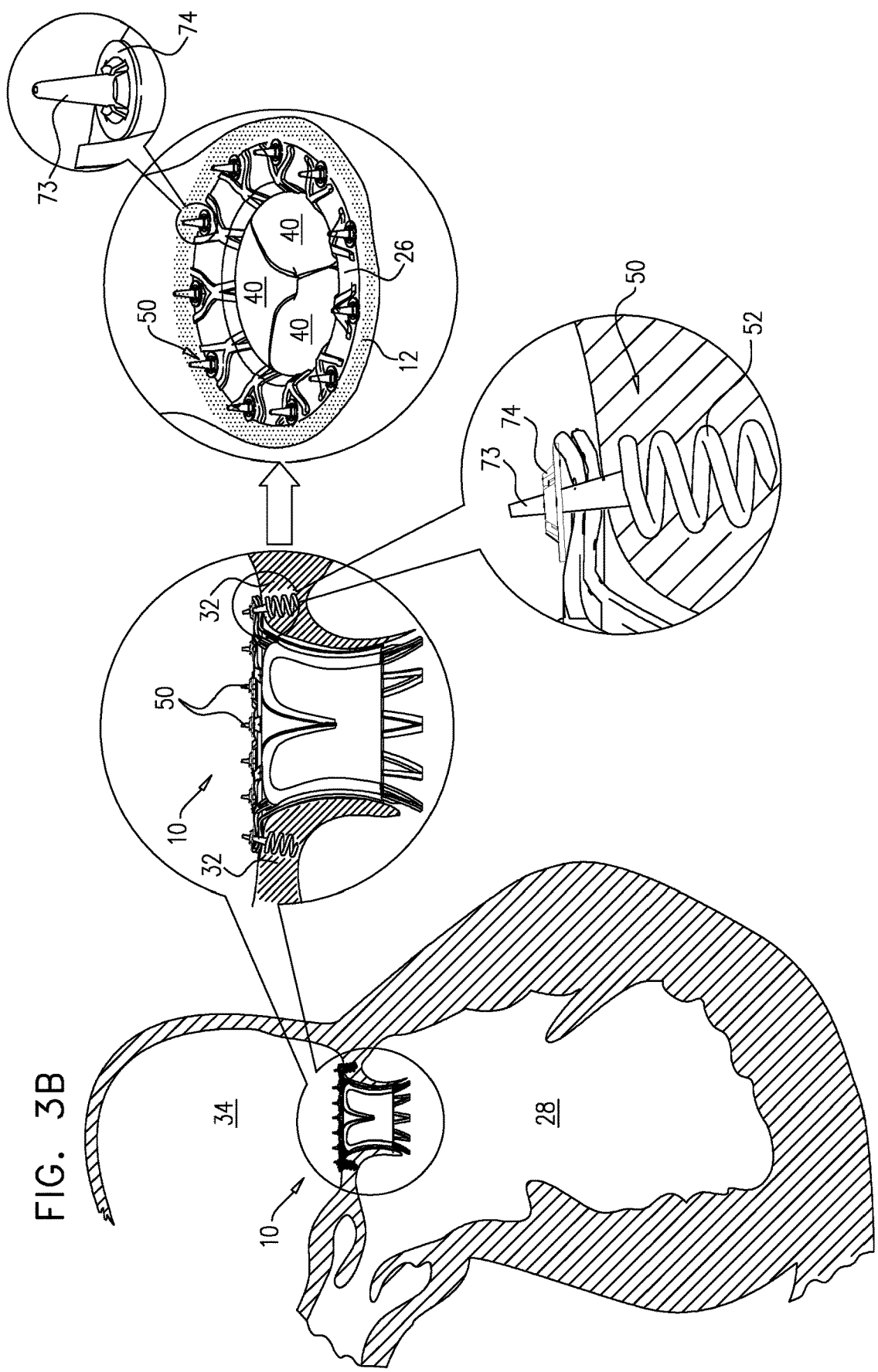

Reference is made to FIGS. 3A-B, which are schematic illustrations of another technique for anchoring prosthetic valve 10 at native valve 12, in accordance with an application of the present invention. In this application, anchors 50 are initially coupled to respective flexible elongated members 70, such as wires, cords, or sutures. For some applications, each of the anchors comprises an upstream post 73, to which a respective elongated member 70 is coupled. Optionally, the posts comprise a flexible material, such as silicone.

As shown in FIG. 3A, during an implantation procedure, the surgeon couples anchors 70 to respective sites of cardiac tissue on native annulus 32. For example, the surgeon may use a rotation tool passed along (e.g., over or alongside) each of elongated members 70.

Subsequently, as shown in FIG. 3B, the surgeon passes prosthetic valve 10 over elongated members 70, until the prosthetic valve reaches the native valve and upstream annular skirt 26 rests against the atrial side of native annulus 32. In order to guide the prosthetic valve to the anchors and desired anatomical position, elongated members 70 pass through respective locations on upstream annular skirt 26. Upstream annular skirt 26 is then coupled to the anchors, e.g., posts 73 thereof, to hold the prosthetic valve in place at the native annulus, creating a seal between the upstream skirt and the native annulus. This anchoring technique typically reshapes the native annulus to assume a rounder shape, similar to that of the prosthetic valve.

For some applications, respective coupling elements 74 are used to couple the skirt to the posts of the anchors. The coupling elements may be passed over elongated members 70. For example, the coupling elements may be shaped as discs with inwardly-facing teeth that engage the posts, and prevent removal of the disc from the posts. The elongated members are subsequently decoupled from anchors 50. For example, a cutting tool may be used to decouple the elongated members from the anchors; the cutting tool may be passed through catheter 72, and/or guided along the elongated member. Alternatively, the elongated members may be looped through the anchors, such that both ends of each elongated member remain outside of the patient's body. The surgeon decouples the elongated member from the anchor by releasing one end of the elongated member and pulling on the other end, until the elongated member is drawn from the anchor.

Figure 4A:
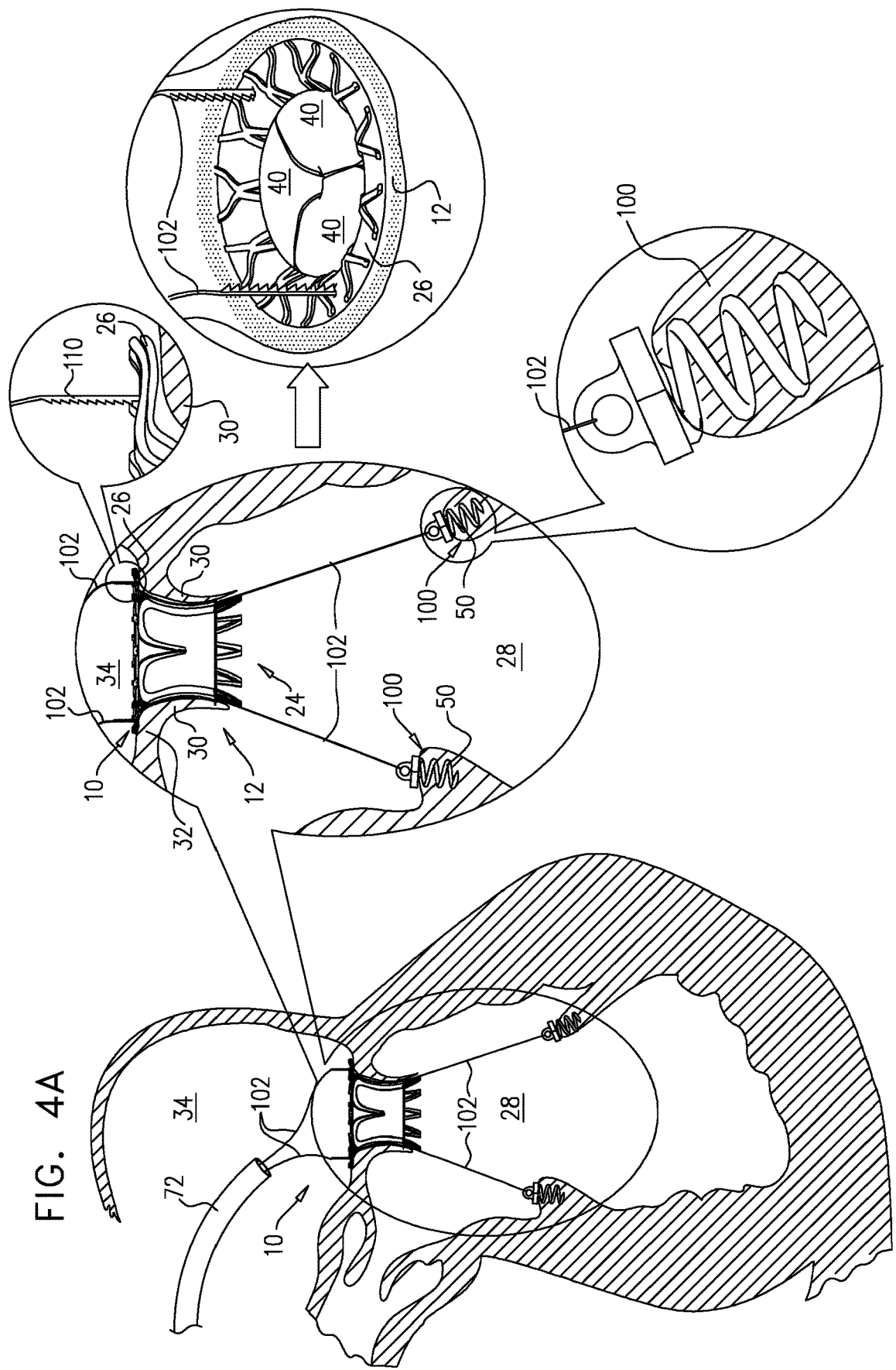
Figure 4B:
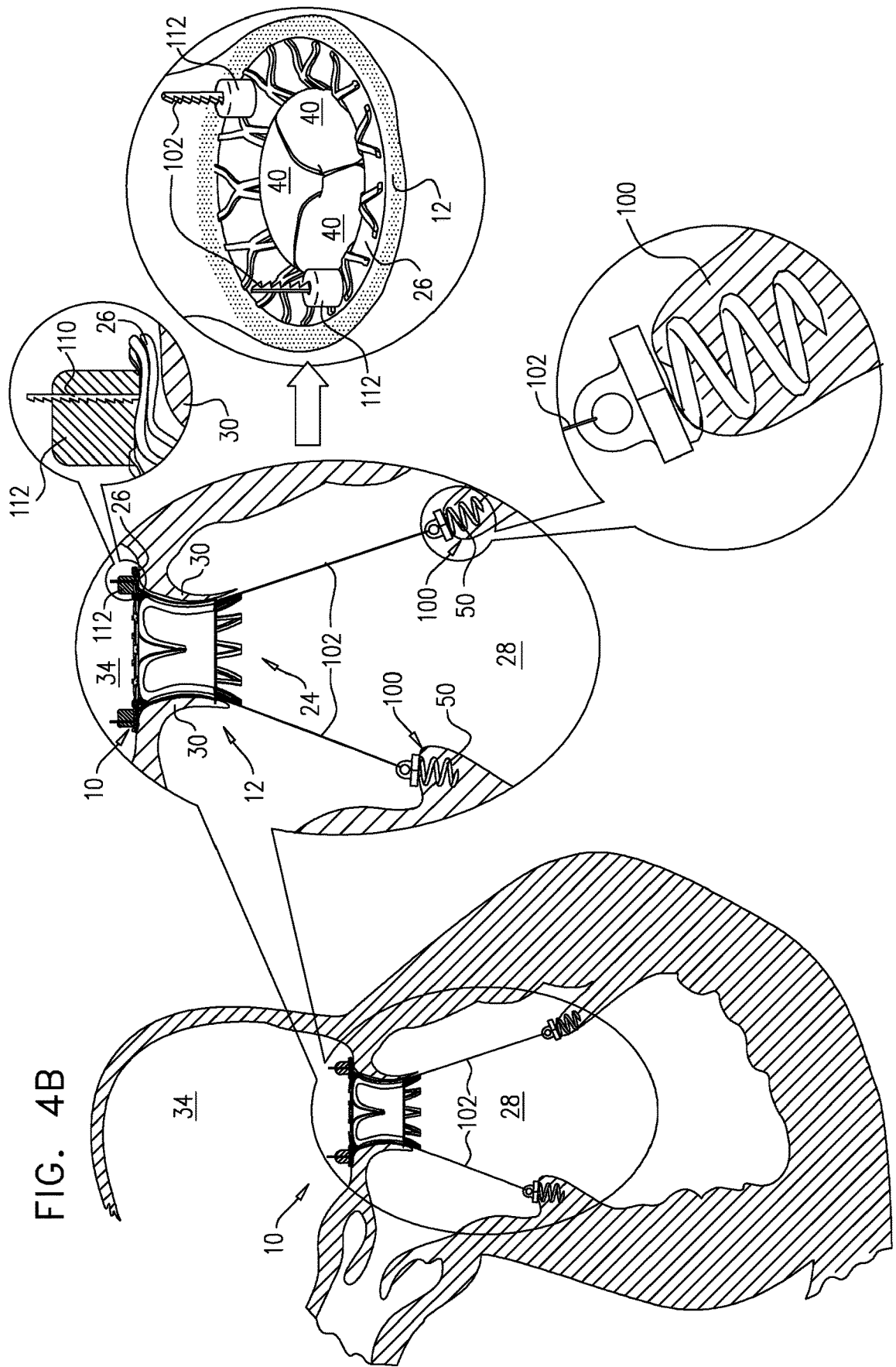

Reference is made to FIGS. 4A-C, which are schematic illustrations of another technique for anchoring prosthetic valve 10 at native valve 12, in accordance with respective applications of the present invention. In these applications, prosthetic valve 10 is held in place at native valve 12 by a ventricular anchoring assembly. The ventricular anchoring assembly comprises one or more ventricular longitudinal members, such as ventricular cords 102, and one or more respective ventricular tissue anchors 50, described hereinabove. The ventricular cords are coupled, using the respective anchors, to respective ventricular sites, such as respective papillary muscles 100 (as shown in FIGS. 4A-C) or other locations of the ventricular wall, such as near the apex of ventricle 28 (configuration not shown). The cords pull prosthetic valve 10 toward ventricle 28, such that upstream annular skirt 26 is pulled tightly against native annulus 32. As mentioned above, the upstream annular skirt is too large to pass through the native annulus, and is thus held in place by the cords.

For some applications, in order to tense ventricular cords 102, prosthetic valve 10 and upstream portions 110 of the cords are configured to provide one-way upstream motion of the cords with respect to the prosthetic valve, and to prevent distal motion of the cords. For example, upstream portions 110 of the cords may be shaped so as to define a one-way ratchet, which can pass through upstream annular skirt 26 in an upstream direction, but not in a downstream direction. After the cords have been anchored to the ventricular sites and the prosthetic valve has been placed in position at the native annulus, the surgeon pulls upstream on the upstream ends of the cords, in order to tense the cords. Optionally, as shown in FIGS. 4B and 4C, upstream annular skirt 26 comprises ratcheting elements 112, through which ratcheted upstream portions 110 of ventricular cords 102 pass, in order to prevent such downstream motion.

For some applications, in order to provide access to anchors 50 during coupling of the anchors to the ventricular sites, the surgeon first introduces the anchors and cords into the ventricle, thereafter couples the anchors to the ventricular sites, and subsequently positions the prosthetic valve at the native annulus. The cords may pass between downstream skirt 24 and native leaflets 30 (as shown in FIGS. 4A-C), or through the downstream skirt (configuration not shown).

For some applications, as shown in FIG. 4C, the surgeon crosses cords 102 in the ventricle, such that the cords assume an X-shape when viewed from the side. Such crossing may provide firmer anchoring of the prosthetic valve to the native annulus.

For some applications, the coupling techniques described with reference to FIGS. 4A-C effect ventricular remodeling, in addition to or instead of anchoring the prosthetic valve to the native valve site.

For some applications, instead of being coupled to upstream annular skirt 26 (as shown in FIGS. 4A-C), cords 102 are alternatively or additionally coupled to downstream skirt 24, such as to struts of the support frame thereof, e.g., at or near a downstream end of the downstream skirt (configuration not shown).

Figure 5A:
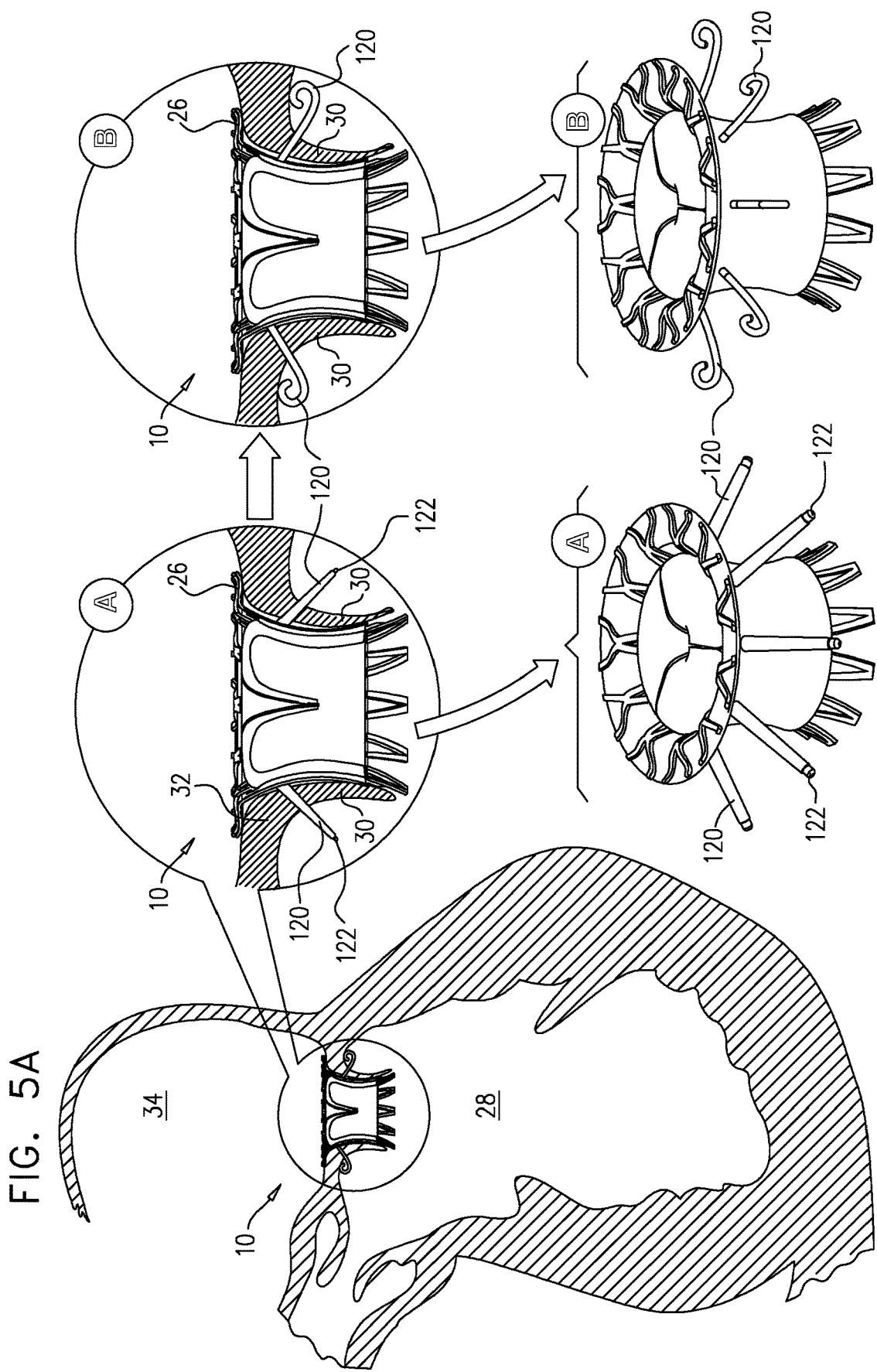
FIGS. 5A-C are schematic illustrations of additional techniques for anchoring the prosthetic valve of FIG. 1 at the native valve, in accordance with respective applications of the present invention.
Figure 5B:
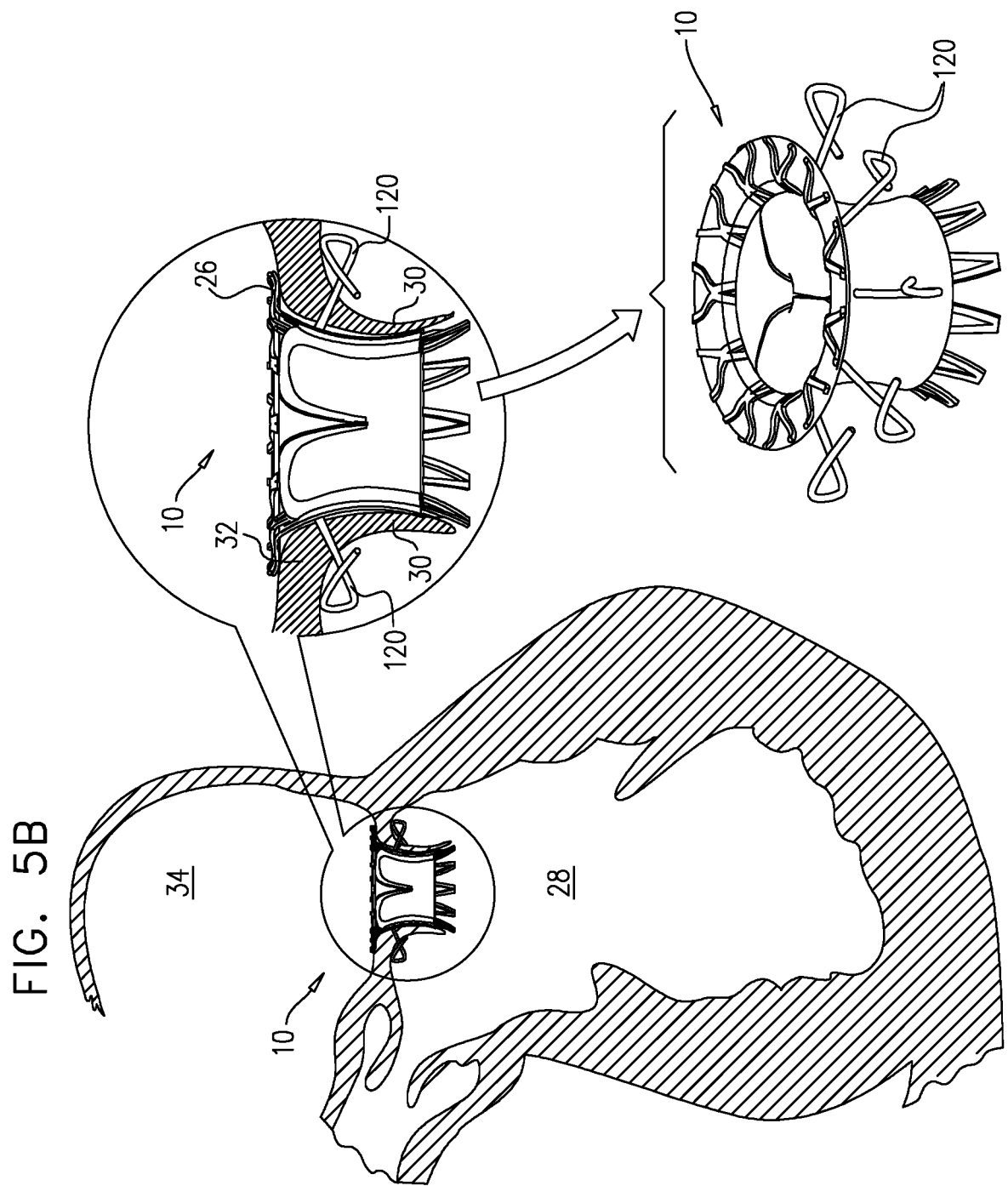
Figure 5C:
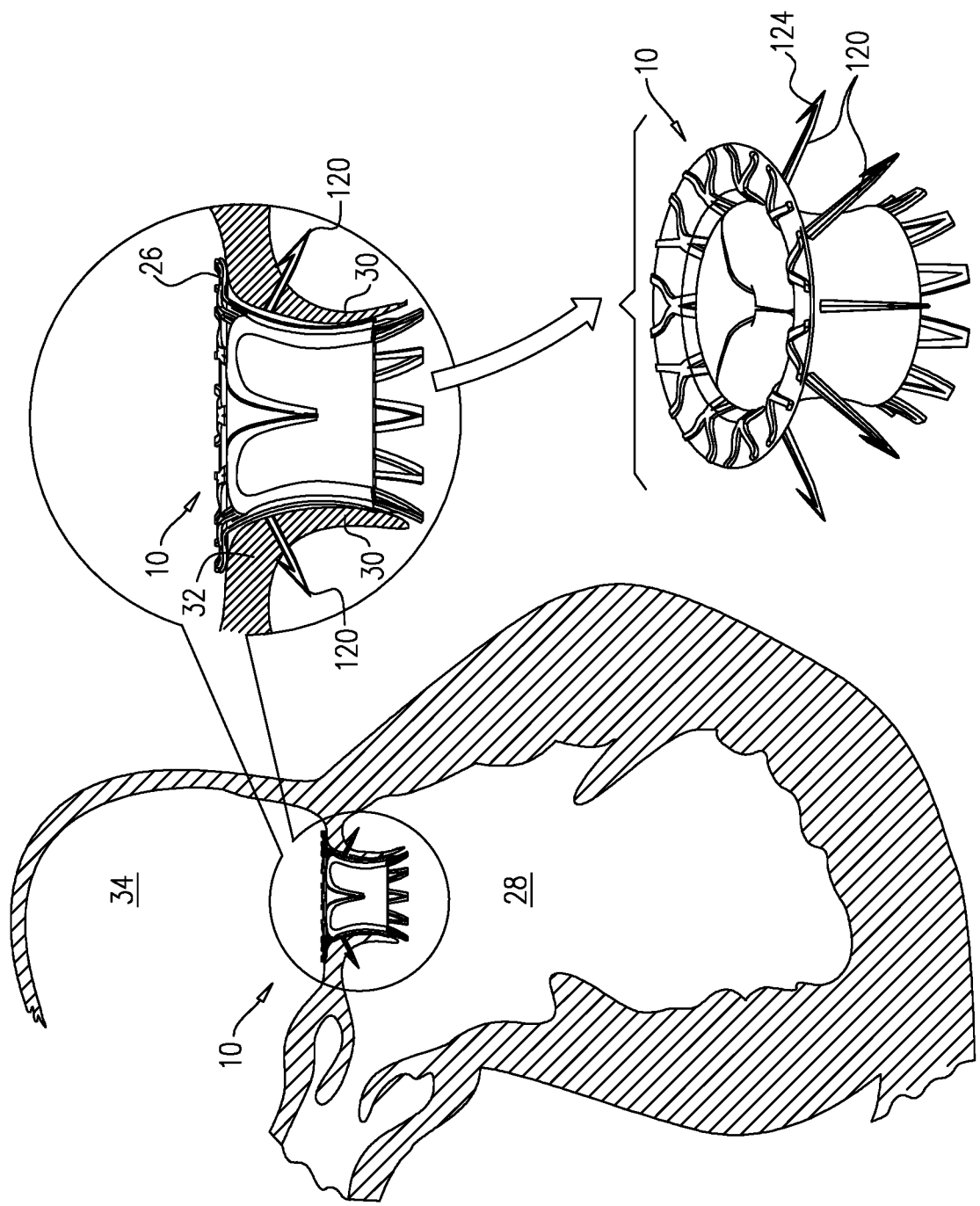

Reference is made to FIGS. 5A-C, which are schematic illustrations of additional techniques for anchoring prosthetic valve 10 at native valve 12, in accordance with respective applications of the present invention. In these applications, prosthetic valve 10 comprises one or more subvalvular anchoring elements 120, which are configured to pierce native leaflets 30 and pass through to a subvalvular space. Anchoring elements 120 are typically shaped and positioned to apply a force against the ventricular surface of native leaflets 30, thereby holding upstream annular skirt 26 against the native annulus. The anchoring elements are generally elongated (e.g., have a length of between 2 and 7 mm), and may, for example, be shaped as hollow needles, solid needles, rods, or rectangular plates. The anchoring elements typically comprise a metal, such as Nitinol.

For some applications, as shown in FIG. 5A, distal ends of anchoring elements 120 are curved toward upstream annular skirt 26, and thus toward the ventricular surface of the native annulus when the prosthetic valve is implanted. For other applications, as shown in FIG. 5B, the distal ends of the anchoring elements are folded. Alternatively or additionally (i.e., optionally in combination with the application shown in FIG. 5A or the application shown in FIG. 5B), the distal ends of the anchoring elements are shaped so as to define respective barbs 124, as shown in FIG. 5C.

For some applications, as shown in FIG. 5A, the anchoring elements are configured to assume a curved shape when in resting states. In order to more readily pierce the native leaflets, the anchoring elements are configured to initially assume a straighter shape during the implantation procedure. For example, as shown as configuration "A" of FIG. 5A, rigid rods 122 may be initially inserted into the lumens of the anchoring elements, which are shaped as hollow needles, in order to at least partially straighten the anchoring elements. After the anchoring elements have penetrated the native leaflets, rods 122 are withdrawn from the anchoring elements, and the anchoring elements assume their curved shapes, as shown as configuration "B" of FIG. 5A. For some applications, an implantation tool is provided that comprises rods 122. This technique may additionally be used in combination with the application shown in FIG. 5B or the application shown in FIG. 5C. Alternatively or additionally, the anchoring elements comprises a shape memory alloy that is configured to initially assume a straighter shape, e.g., at a first temperature, and subsequently a curved shape, e.g., at a second temperature.

Figure 6:
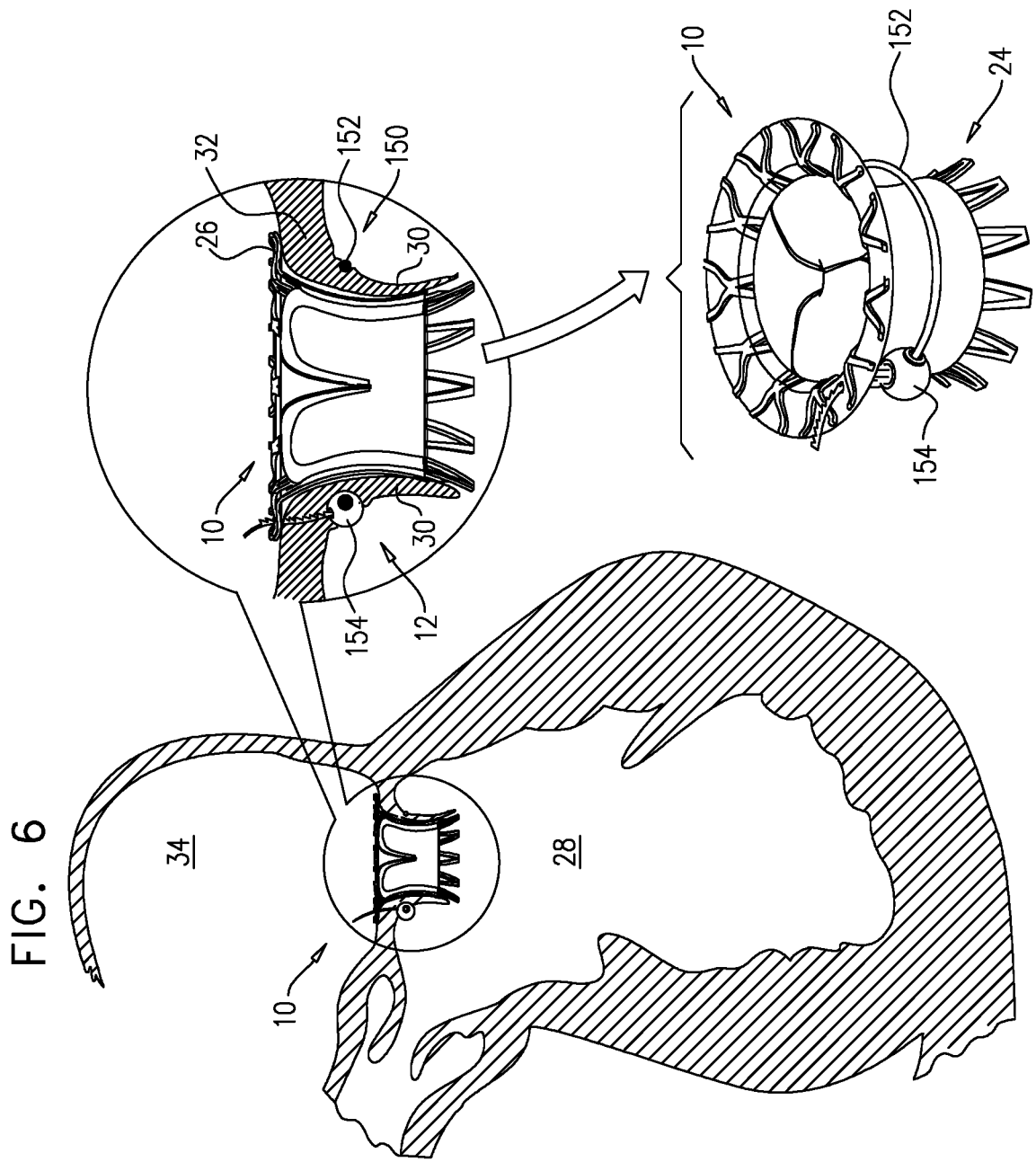
FIG. 6 is a schematic illustration of yet another technique for anchoring the prosthetic valve of FIG. 1 at the native valve, in accordance with an application of the present invention.

Reference is made to FIG. 6, which is a schematic illustration of yet another technique for anchoring prosthetic valve 10 at native valve 12, in accordance with an application of the present invention. In this application, prosthetic valve 10 comprises an elongated anchoring member 152, such as a cord, strip, wire, or suture. Anchoring member 152 is configured to be positioned around at least a radial portion of downstream skirt 24 and be positioned in a subvalvular space 150. When tightened, the anchoring member squeezes native leaflets 30 against downstream skirt 24, thereby fixing prosthetic valve 10 in place at the native valve, and creating a seal between the valve prosthesis and the native leaflets. For some applications, anchoring member 152 is positioned completely around, i.e., surrounds, downstream skirt 24. For some applications, the anchoring member is introduced into the subvalvular space and brought around the native leaflets using a guidewire that is introduced around the leaflets tangential to native annulus 32.

For some applications, valve prosthesis 10 further comprises a contracting housing 154. Typically, a first end of anchoring member 152 is fixed to the contracting housing, and a second end of the anchoring member passes through a channel of the contracting housing. Pulling on the second end of the anchoring member tightens the anchoring member around the native leaflets. For some applications, an upstream portion of the anchoring member is shaped so as to define a ratchet, which allows tightening, but not loosening, of the anchoring member.

Figure 7:
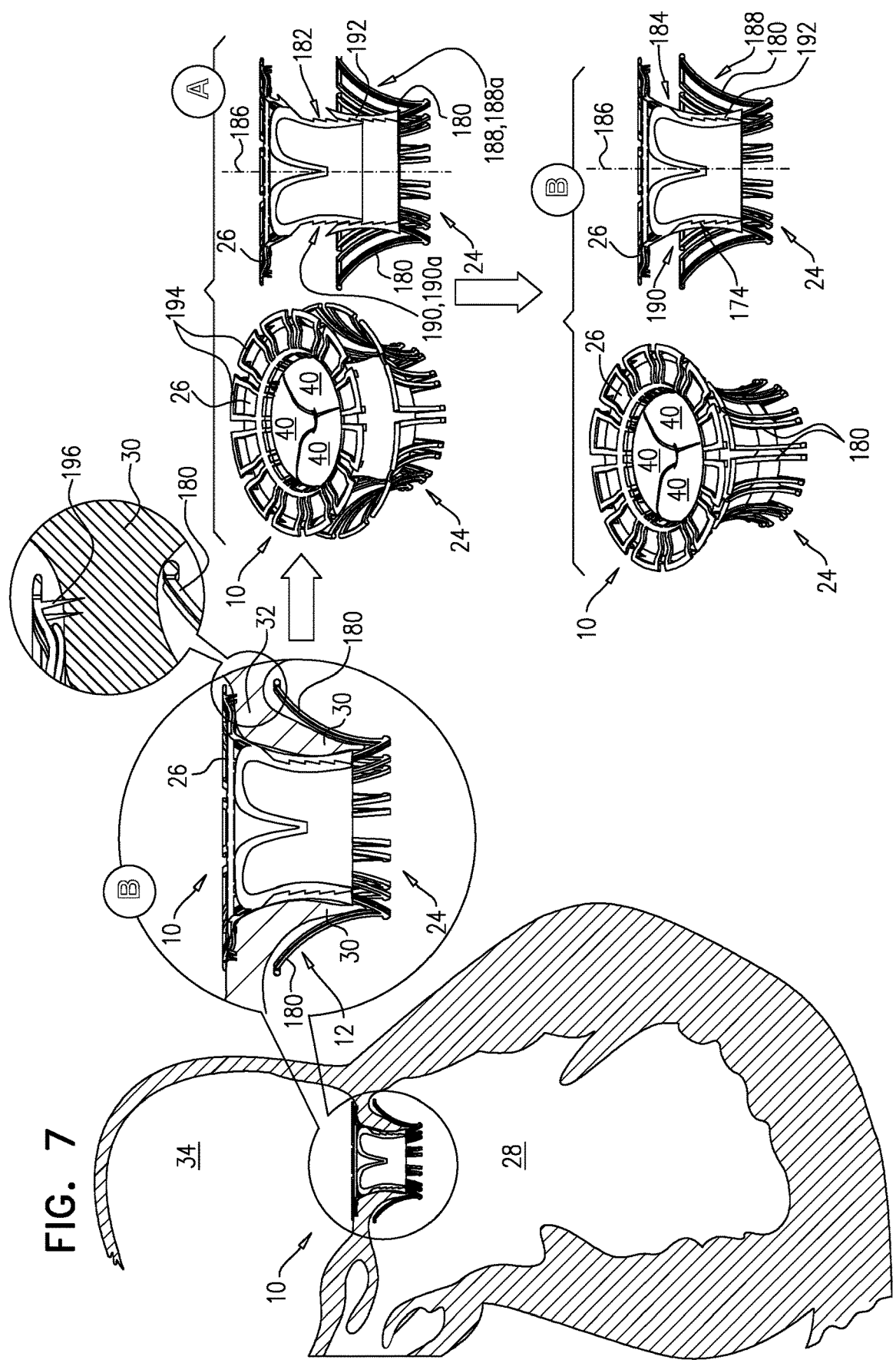
FIG. 7 is a schematic illustration of still another technique for anchoring the prosthetic valve of FIG. 1 at the native valve, in accordance with an application of the present invention.

Reference is made to FIG. 7. which is a schematic illustration of still another technique for anchoring prosthetic valve 10 at native valve 12, in accordance with an application of the present invention. In this application, downstream skirt 24 is shaped so as to define a plurality of anchoring arms 180, which extend in an upstream direction from a downstream end of downstream skirt 24 (as shown in FIG. 7), or from locations near the downstream end of the downstream skirt (configuration not shown). The coupling arms are configured to be positioned in the subvalvular space.

Prosthetic valve 10 is configured to assume two states: (a) an extended, unlocked state 182, shown as configuration "A" of FIG. 7, and (b) a contracted, locked state 184, shown as configuration "B" of FIG. 7. A longitudinal length of prosthetic valve 10 along a central longitudinal axis 186 thereof is greater when the prosthetic valve is in extended, unlocked state 182, than when the prosthetic valve is in contracted, locked state 184. The prosthetic valve is typically configured to allow one-way passage from unlocked state 182 to locked state 184. For example, mating downstream and upstream portions 188 and 190 of downstream skirt 24 may be shaped so as to define corresponding ratchet teeth 192, which allow downstream portion 188 to move in an upstream direction with respect to upstream portion 190, but not in a downstream direction with respect thereto. (In this regard, upstream portion 190 is a first portion 190a of the downstream skirt, and downstream portion 188 is a second portion 188a of the downstream skirt.)

During an implantation procedure, prosthetic valve 10 initially assumes extended, unlocked state 182. The prosthetic valve is advanced to native valve 12 in this unlocked state, and anchoring arms 180 are positioned such that native leaflets 30 are between the anchoring arms and the body of downstream skirt 24. The surgeon causes the prosthetic valve to assume contracted, locked state 184. In locked state 184 the anchoring arms squeeze and grasp native leaflets 30 and a portion of native annulus 32 between the anchoring arms, the body of the downstream skirt 24, and upstream annular skirt 26. In this application, upstream annular skirt 26 may comprise relative short upstream arms 194, which may correspond to and be aligned with anchoring arms 180 of downstream skirt 24. Optionally, upstream arms 194 may comprise one or more spikes 196, which are configured to pierce native annulus 32 in order to aid with anchoring.

FIGS. 8A-G are schematic illustrations of a valve contraction tool 200 and a procedure for the use thereof, in accordance with an application of the present invention. Valve contraction tool 200 is optionally used with the configuration of prosthetic valve 10 described hereinabove with reference to FIG. 7, in order to cause prosthetic valve 10 to transition from extended, unlocked state 182 to contracted, locked state 184.

Figure 8A:
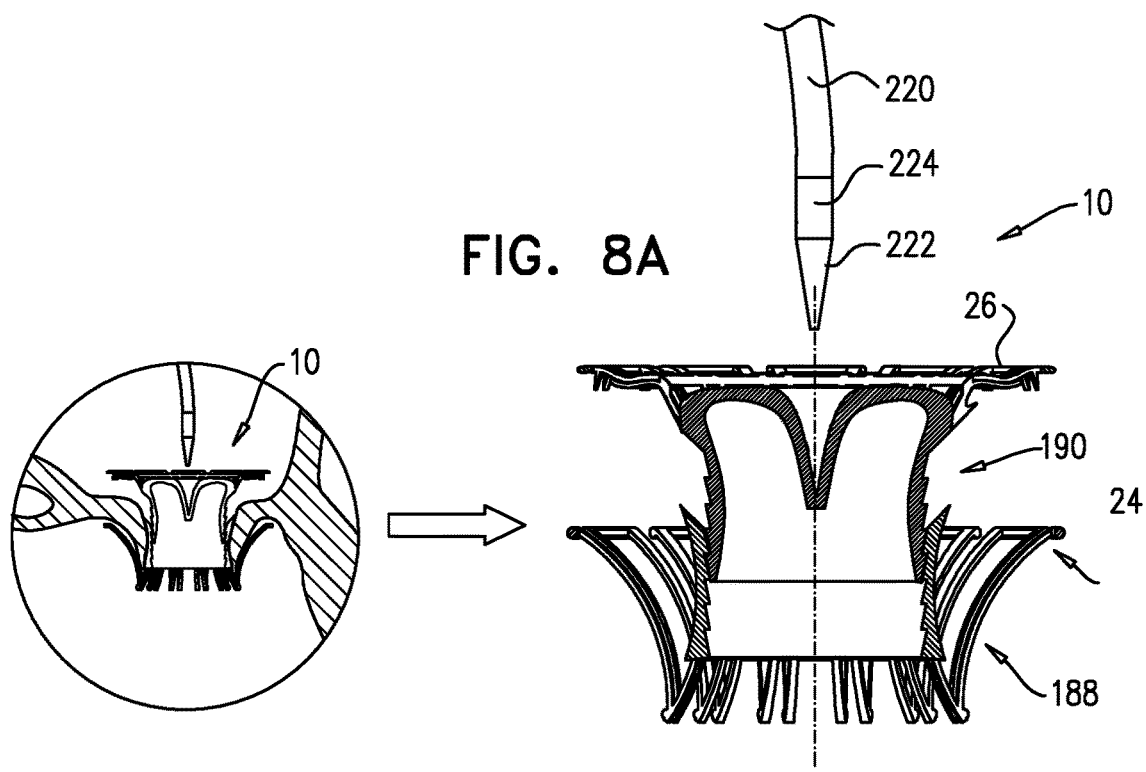
Figure 8B:
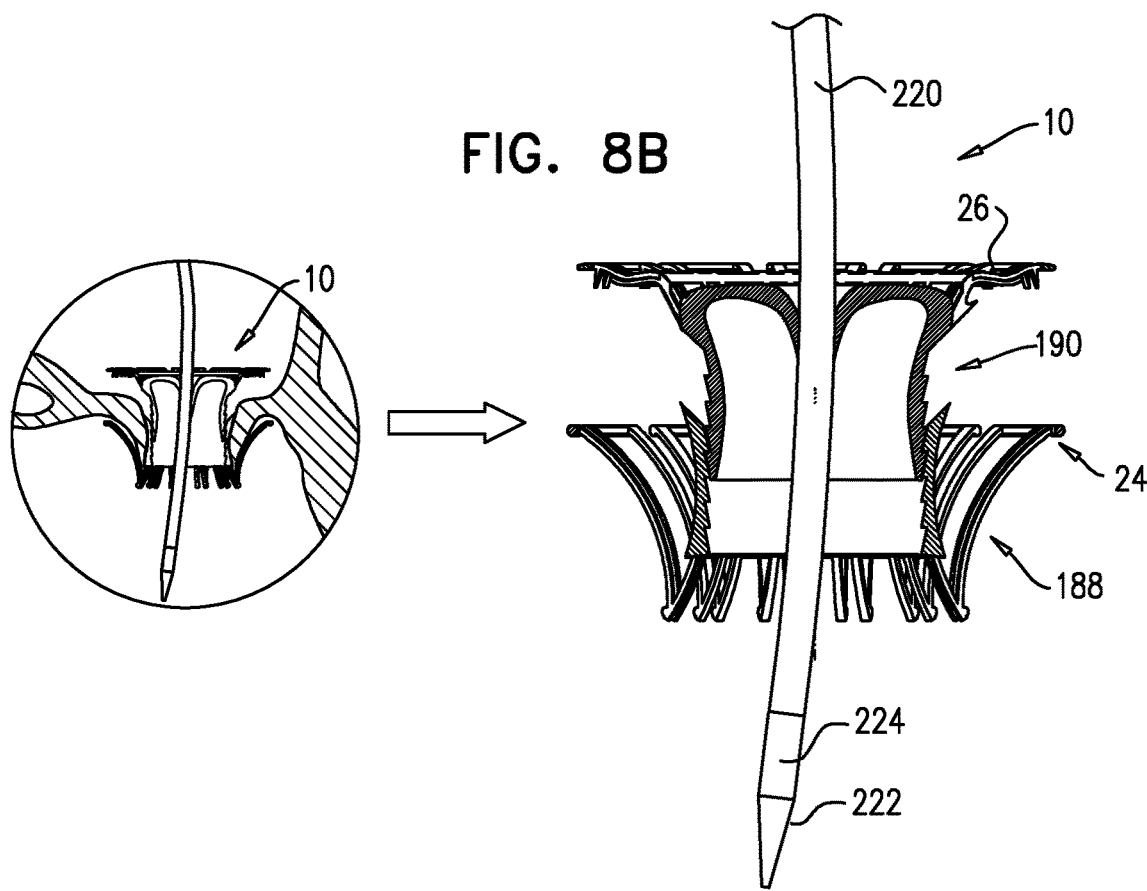
Figure 8E:
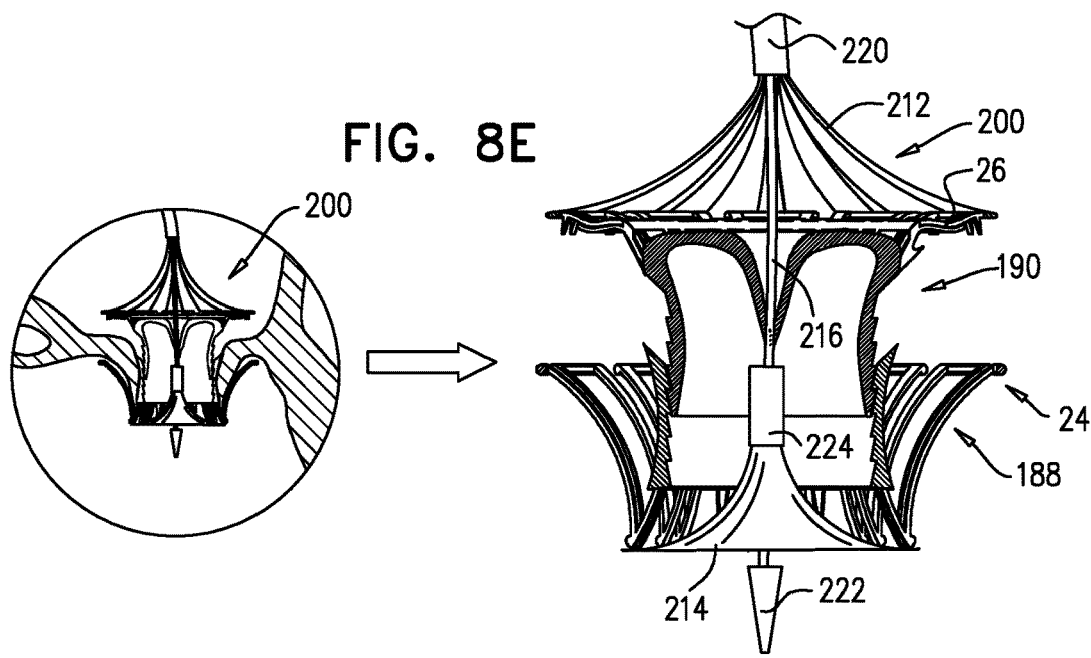

As best seen in FIG. 8E, tool 200 comprises a catheter 220, and an upstream pushing tube (not shown), a downstream end of which is coupled to an upstream pushing adaptor 212. Upstream pushing adaptor 212 is configured to assume an umbrella-like shape when expanded, forming a downstream ring that is sized to rest and push against upstream annular skirt 26. Tool 200 further comprises a downstream pulling adaptor 214, which is coupled to a pulling wire 216. Downstream pulling adaptor 214 is configured to rest against the downstream end of downstream skirt 24. Pulling wire 216 is coupled to the downstream pulling adaptor (e.g., at a center thereof), and passes through upstream pushing adaptor 212 and the upstream pushing tube.

For some applications, a procedure using tool 200 begins with the introduction of catheter 220, as shown in FIG. 8A. Catheter 220 is advanced through the lumen of prosthetic valve 10, until a downstream cap 222 of the catheter passes entirely through the prosthetic valve, as shown in FIG. 8B.

As shown in FIG. 8C, downstream cap 222 is extended downstream from a downstream adaptor holder 224, releasing downstream pulling adaptor 214 from downstream adaptor holder 224. Upon release, downstream pulling adaptor 214 expands. Pulling wire 216 is pulled in an upstream direction, pulling downstream pulling adaptor 214 against downstream portion 188 of downstream skirt 24, as shown in FIG. 8D.

As shown in FIG. 8E, upstream pushing adaptor 212 is deployed from catheter 220 against upstream annular skirt 26. In order to longitudinally contract prosthetic valve 10, the surgeon pulls pulling wire 216 in an upstream direction, while simultaneously pushing on the pushing tube in a downstream direction. The pushing tube pushes upstream pushing adaptor 212 against upstream annular skirt 26, thereby holding the annular skirt against native annulus 32, and holding upstream portion 190 of downstream skirt 24 stationary. Pulling wire 216 pulls on downstream pulling adaptor 214, causing the downstream pulling adaptor to pull downstream portion 188 of downstream skirt 24 toward upstream portion 190, thereby contracting the prosthetic valve.

Figure 8F:
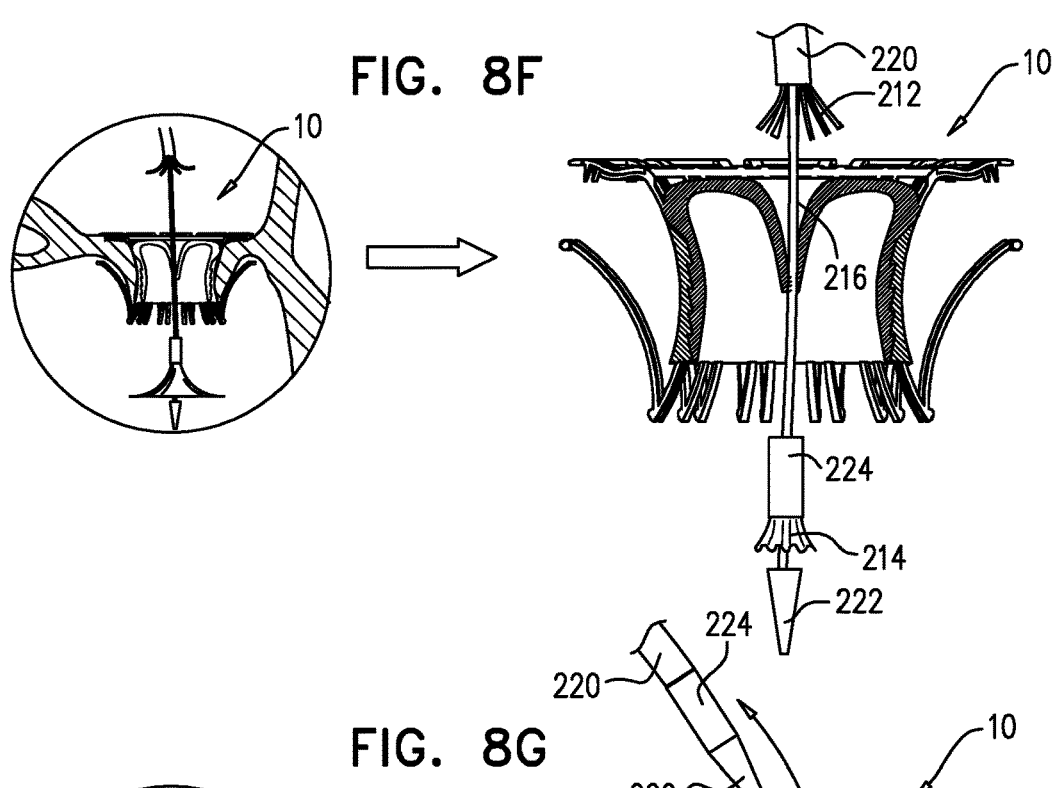
Figure 8G:
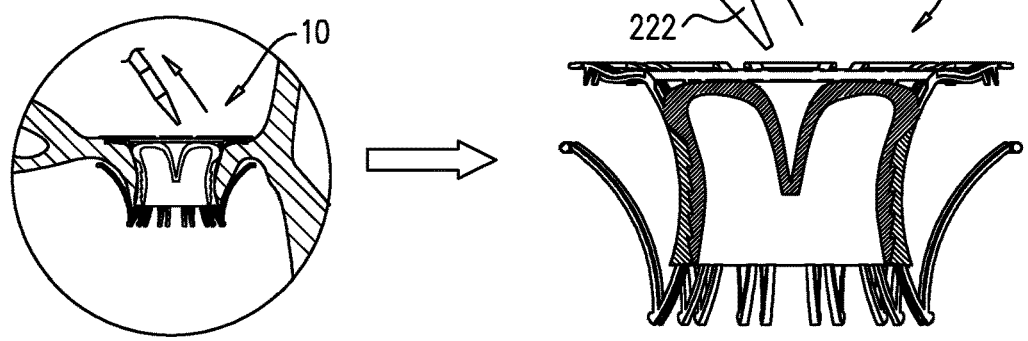

Upstream pushing adaptor 212 is retracted into catheter 220, and downstream pulling adaptor 214 is retracted into downstream adaptor holder 224, as shown in FIG. 8F. Pulling wire 216 pulls adaptor holder 224 and downstream cap 222 against the body of catheter 220, and the catheter is withdrawn from prosthetic valve 10, as shown in FIG. 8G.

Although prosthetic valve 10 has been described herein as being configured for implantation in and/or at least partial replacement of a native atrioventricular valve, for some applications prosthetic valve 10 is configured for implantation in and/or at least partial replacement of a native aortic valve or a native pulmonary valve, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use at an atrioventricular valve that has an annulus and is disposed between an atrium and a ventricle of a heart of a subject, the method comprising:
    transluminally advancing a catheter to the heart;
    via the catheter, advancing to the heart a prosthetic valve including:
        an upstream annular skirt,
        a downstream skirt having:
            a first portion defining a lumen therethrough, and
            a second portion circumscribing the first portion,
        a plurality of anchoring arms, each of the anchoring arms having a first end that is coupled to the second portion, and an opposite end that is a free end, and
        a plurality of prosthetic leaflets attached to the first portion and disposed within the lumen;
    expanding the upstream annular skirt in the atrium and expanding the anchoring arms in the ventricle such that:
        the upstream annular skirt becomes disposed over the annulus, and
        each of the anchoring arms becomes oriented to lead in a direction from the first end to the opposite end, the direction being radially outward and toward the upstream annular skirt; and
    subsequently to expanding the upstream annular skirt in the atrium, and while each of the anchoring arms remains oriented to lead in the direction from the first end to the opposite end, squeezing tissue of the atrioventricular valve between the upstream annular skirt and the anchoring arms by causing the second portion of the downstream skirt and the anchoring arms to move:
        (i) with respect to the prosthetic leaflets, and
        (ii) toward the upstream annular skirt.

2. The method according to claim 1, wherein:
    the first end of each of the anchoring arms is coupled to a downstream portion of the second portion, and
    advancing the prosthetic valve comprises advancing the prosthetic valve in which the first end of each of the anchoring arms is coupled to the downstream portion of the second portion.

3. The method according to claim 2, wherein:
    the first end of each of the anchoring arms is coupled to a downstream end of the second portion, and
    advancing the prosthetic valve comprises advancing the prosthetic valve in which the first end of each of the anchoring arms is coupled to the downstream end of the second portion.

4. The method according to claim 1, wherein causing the second portion of the downstream skirt and the anchoring arms to move with respect to the leaflets and toward the upstream annular skirt comprises causing the prosthetic valve to move from an extended, unlocked state into a contracted, locked state.

5. The method according to claim 1, wherein the downstream skirt defines a plurality of ratchet teeth, and causing the second portion of the downstream skirt and the anchoring arms to move with respect to the leaflets and toward the upstream annular skirt comprises causing mating between ratchet teeth of the plurality of ratchet teeth.

6. The method according to claim 1, wherein the upstream annular skirt includes a plurality of skirt arms, and expanding the upstream support portion in the atrium comprises expanding the upstream support portion in the atrium such that the plurality of skirt arms extend radially outward.

7. The method according to claim 6, wherein each skirt arm is aligned with a respective one of the anchoring arms, and causing the anchoring arms to move with respect to the leaflets and toward the upstream annular skirt comprises causing each skirt arm to become closer to its respective one of the anchoring arms.

8. The method according to claim 7, wherein the upstream annular skirt includes exactly 12 skirt arms, and the second portion of the downstream skirt defines exactly 12 anchoring arms.

9. The method according to claim 1, wherein causing the second portion of the downstream skirt and the anchoring arms to move with respect to the leaflets and toward the upstream annular skirt comprises using a tool to apply (i) an upstream force to the downstream skirt, and (ii) a downstream force to the upstream annular skirt.

10. The method according to claim 9, further comprising expanding an upstream adapter of the tool, and expanding a downstream adapter of the tool, wherein using the tool to apply the upstream force and the downstream force comprises (i) using the downstream adapter to apply the upstream force to the downstream skirt, and (ii) using the upstream adapter to apply the downstream force to the upstream annular skirt.

11. The method according to claim 9, wherein the method further comprises, subsequently to expanding the upstream annular skirt in the atrium and expanding the anchoring arms in the ventricle, transluminally advancing the tool to the prosthetic valve.

12. The method according to claim 11, wherein transluminally advancing the tool to the prosthetic valve comprises transluminally advancing the downstream adapter through the lumen of the first portion.

13. The method according to claim 1, further comprising advancing a tool via the catheter to the heart, such that a downstream portion of the tool is disposed within the ventricle downstream of the prosthetic valve, and wherein causing the second portion of the downstream skirt and the anchoring arms to move with respect to the leaflets and toward the upstream annular skirt comprises causing the second portion of the downstream skirt and the anchoring arms to move with respect to the leaflets and toward the upstream annular skirt by moving the downstream portion of the tool longitudinally with respect to the prosthetic valve.

14. The method according to claim 13, wherein the downstream portion of the tool comprises a downstream cap.

* * * * *